(12) United States Patent
Liang et al.

(10) Patent No.: US 7,022,337 B2
(45) Date of Patent: Apr. 4, 2006

(54) SELF-EMULSIFYING FORMULATIONS OF FENOFIBRATE AND/OR FENOFIBRATE DERIVATIVES WITH IMPROVED ORAL BIOAVAILABILITY AND/OR REDUCED FOOD EFFECT

(75) Inventors: Likan Liang, Germantown, MD (US); Amir H. Shojaei, Gaithersburg, MD (US); Scott A. Ibrahim, Ellicott City, MD (US); Beth A. Burnside, Bethesda, MD (US)

(73) Assignee: Shire Laboratories, Inc., Rockville, MD (US)

( * ) Notice: Subject to any disclaimer, the term of this patent is extended or adjusted under 35 U.S.C. 154(b) by 0 days.

(21) Appl. No.: 10/607,719

(22) Filed: Jun. 27, 2003

(65) Prior Publication Data
US 2004/0110842 A1 Jun. 10, 2004

Related U.S. Application Data

(63) Continuation-in-part of application No. 10/324,953, filed on Dec. 20, 2002.

(60) Provisional application No. 60/392,791, filed on Jun. 28, 2002.

(51) Int. Cl.
*A61K 9/48* (2006.01)
(52) U.S. Cl. .................................. 424/451; 424/452
(58) Field of Classification Search ............... 424/450, 424/451, 455, 489, 452
See application file for complete search history.

(56) References Cited

U.S. PATENT DOCUMENTS

| | | | |
|---|---|---|---|
| 4,397,848 A * | 8/1983 | Bosies et al. ............... 514/183 |
| 4,895,726 A | 1/1990 | Curtet et al. |
| 5,545,628 A * | 8/1996 | Deboeck et al. .............. 514/49 |
| 5,741,512 A * | 4/1998 | Hauer et al. ................ 424/450 |
| 5,776,957 A * | 7/1998 | Crooks et al. .............. 514/343 |
| 5,827,536 A * | 10/1998 | Laruelle ..................... 424/451 |
| 6,074,670 A | 6/2000 | Stamm et al. |
| 6,174,547 B1 * | 1/2001 | Dong et al. .................. 424/463 |
| 6,267,985 B1 * | 7/2001 | Chen et al. ................. 424/451 |
| 2002/0032220 A1 * | 3/2002 | Al-Ghazawi et al. ........ 514/321 |

FOREIGN PATENT DOCUMENTS

WO   WO 99/29300 A1 *  6/1999

* cited by examiner

*Primary Examiner*—Susan T. Tran
*Assistant Examiner*—S. Tran
(74) *Attorney, Agent, or Firm*—Raj Bawa

(57) ABSTRACT

A fibrate self-emulsifying oral formulation with improved bioavailability when compared to commercially available formulations containing a therapeutically effective dose of fenofibrate, derivative of fenofibrate or mixtures thereof dissolved in a fibrate solubilizer selected from N-alkyl derivative of 2-pyrrolidone, mono- or di- or polyethylene glycol monoethers, $C_{8-12}$ fatty acid mono- or di-esters of propylene glycol, or combinations thereof, one or more surfactants and optionally one or more stabilizers useful in the treatment of hypercholesterolaemia or hypertriglyceridaemia in mammals in the fed or fasted state.

19 Claims, No Drawings

SELF-EMULSIFYING FORMULATIONS OF FENOFIBRATE AND/OR FENOFIBRATE DERIVATIVES WITH IMPROVED ORAL BIOAVAILABILITY AND/OR REDUCED FOOD EFFECT

This application is a continuation-in-part of Ser. No. 10/324,953 filed Dec. 20, 2002 which claims benefit of 60/392,791 filed Jun. 28, 2002.

FIELD OF THE INVENTION

The present invention relates to a non-aqueous self-emulsifying oral pharmaceutical formulations of fenofibrate or fenofibrate derivatives having an improved oral bioavailability and/or reduced food effect when compared to a commercial available formulation.

BACKGROUND OF THE INVENTION

Fenofibrate is a fibrate used in the treatment of endogenous hyperlipidaemias, hypercholesterolaemias and hypertriglyceridaemias in adults. The preparation of fenofibrate is disclosed in U.S. Pat. No. 4,058,552. Fenofibric acid, the active metabolite of fenofibrate, produces reductions in total cholesterol, LDL cholesterol, apolipoprotein B, total triglycerides and triglyceride rich lipoprotein (VLDL) in treated patients. Also, treatment with fenofibrate results in increases in high-density lipoprotein (HDL) and apoproteins apoAI and apoAII. Prolonged treatment with fenofibrate at the rate of 300 to 400 mg per day makes it possible to obtain a reduction in total cholesterol of 20 to 25% and a reduction in the levels of triglycerides of 40 to 50%. It thus opposes the development of arteriosclerosis. The customary adult fenofibrate dosage is three gelatin capsules per day, each containing 100 mg of fenofibrate. It is known that fenofibrate absorption variations are observed depending on whether the drug was ingested with a high or low fat meal (Atkins J. C. and D. Faulds (1997) Drugs 54(4) 615–633).

Fenofibrate is not soluble in water, which limits its absorption in the gastrointestinal (GI) tract. To remedy this problem, research groups have tried a multitude of strategies. In U.S. Pat. Nos. 4,800,079 and 4,895,726 micronized fenofibrate formulations of are disclosed. In U.S. Pat. No. 6,277,405 the immediate release of micronized fenofibrate in a tablet or in the form of granules inside a capsule is shown. In U.S. Pat. No. 6,074,670 the immediate release of micronized fenofibrate in a solid state is shown. In U.S. Pat. No. 5,880,148 the combination of fenofibrate and vitamin E is discussed, this formulation is claimed to be useful as an antiatheromatous drug and exhibit a synergistic effect in regards to protecting low-density lipoproteins (LDL) from oxidation. In U.S. Pat. No. 5,827,536 the use of diethylene glycol monoethyl ether (DGME) as solubilizer is discussed and an enhancement in bioavailability claimed. In U.S. Pat. No. 5,545,628 the combination of fenofibrate with one or more polyglycolyzed glycerides is disclosed.

To reduce the effect of fatty food on the adsorption of fenofibrate combinations of micronized fibrate and statins have been developed (US patent application publication 20020161032). It is also known that reducing the particle size of fenofibrate reduces the food effect on fenofibrate adsorption.

In order to prepare the solid formulations of Fenofibrate, the compound is normally dissolved in a proper solvent or solubilizers. Fenofibrate is known to be soluble in many different solubilizers, including anionic (e.g. SDS) and non-ionic (e.g. Triton X-100) surfactants, complexing agents (N-methyl pyrrolidone) (Temeljotov et al (1995) Farmacevtski Vestnik (Slovenia), 46/(Special Issue)).

The technology developed to increase the bioavailability of fenofibrate includes elements and process steps that increase the cost of production making them commercially unattractive. If a formulation for the use fenofibrate and its method of preparation of said formulation could be simplified while increasing the bioavailability of fenofibrate, the resulting product would satisfy an existing need in this field. The present invention provides such a product, a liquid or semi-solid formulation with improved bioavailability for oral administration of fenofibrate or fenofibrate derivatives wherein the particle size of the active agent is not critical to the bioavailability of the product.

SUMMARY OF THE INVENTION

The object of the present invention includes an oral self-emulsifying pharmaceutical formulation with improved bioavailability when compared to a commercial available formulation comprising a therapeutically effective amount of the a fibrate dissolved in N-alkyl derivative of 2-pyrrolidone, mono- or di- or poly-ethylene glycol monoethers, $C_{8-12}$ fatty acid mono- or di-esters of propylene glycol, or combinations thereof in the presence of a surfactant or combination of surfactants. The present invention additionally includes oral pharmaceutical self-emulsifying formulations with improved bioavailability comprising a therapeutically effective amount of fenofibrate or a fenofibrate derivative in a N-alkyl derivative of 2-pyrrolidone, mono- or di- or poly-ethylene glycol monoethers, $C_{8-12}$ fatty acid mono- or di-esters of propylene glycol, or combinations thereof in the presence of a surfactant or combination of surfactants wherein the bioavailability of the fibrate or the absorption of the fibrate in fasted patients is improved when compared to a commercial available formulation such as Lipanthyl® (trade mark of Groupe Fournier) or TriCor® (trade mark of Abbott Laboratories).

In an alternate embodiment of the invention a fibrate pharmaceutical self-emulsifying formulation containing a therapeutically effective amount of the fenofibrate or its derivatives dissolved in N-alkyl derivative of 2-pyrrolidone, mono- or di- or poly-ethylene glycol monoethers, $C_{8-12}$ fatty acid mono- or di-esters of propylene glycol, or combinations thereof and at least one surfactant selected from nonionic, anionic, cationic, and zwitterionic surfactants and combinations thereof is disclosed.

The present invention provides for an oral self-emulsifying pharmaceutical formulation with improved bioavailability when compared to a commercial available formulation comprising a therapeutically effective amount of the a fibrate dissolved in fibrate solubilizer selected from N-alkyl derivative of 2-pyrrolidone, mono- or di- or poly-ethylene glycol monoethers, $C_{8-12}$ fatty acid mono- or di-esters of propylene glycol, or combinations thereof in the presence of a surfactant or combination of surfactants wherein the fibrate to fibrate solubilizer weight ratio is between about 1:1 and about 1:100 and the improvement in $C_{max}$ is at least 1.2 times than that for commercial formulation and/or the $AUC_{0-\infty}$ improvement is at least 1.5 times that of commercial formulation such as Lipanthyl® (trade mark of Groupe Fournier) or TriCor® (trade mark of Abbott Laboratories) when dosed in the fasted state. The present invention also includes formulations wherein the concentration of the fibrate is above the saturation point of N-alkyl derivative of 2-pyrrolidone, mono- or di-ethylene glycol monoethers, C8-12 fatty acid mono- or di-esters of propylene glycol, or combinations thereof and the stabilizer is present in sufficient amounts to inhibit the fibrate crystallization.

In an alternate embodiment of the invention a fibrate pharmaceutical self-emulsifying formulation containing a therapeutically effective amount of the fenofibrate or its derivatives dissolved in N-alkyl derivative of 2-pyrrolidone, mono- or di- or poly-ethylene glycol monoethers, $C_{8-12}$ fatty acid mono- or di-esters of propylene glycol, or combinations thereof and at least one surfactant selected from non-ionic, anionic, cationic, and zwitterionic surfactants or combinations thereof, and one or more stabilizers selected from fatty acids, fatty alcohols, alcohols, long chain fatty acid esters, long chain ethers, hydrophilic derivatives of fatty acids, polyvinylpyrrolidones, polyvinylethers, polyvinyl alcohols, hydrocarbons, hydrophobic polymers, moisture-absorbing polymers.

The present invention includes an self-emulsifying oral pharmaceutical formulation with improved bioavailability comprising a therapeutically effective amount of fenofibrate or a fenofibrate derivative, at least one non-ionic hydrophobic surfactant or ionic surfactant or combinations thereof and a fibrate solubilizer selected from N—$C_{1-4}$ alkyl derivative of 2-pyrrolidone, mono- or di- or poly-ethylene glycol monoethers, $C_{8-12}$ fatty acid mono- or di-esters of propylene glycol, or combinations thereof wherein the fibrate to fibrate solubilizer weight ratio is between about 1:1 and about 1:100 and optionally one or more stabilizers selected from fatty acids, fatty alcohols, alcohols, long chain fatty acid esters, long chain ethers, hydrophilic derivatives of fatty acids, polyvinylpyrrolidones, polyvinylethers, polyvinyl alcohols, hydrocarbons, hydrophobic polymers, moisture-absorbing polymers. The present invention includes formulations where in the concentration of the fibrate is above the saturation point of the selected fibrate solubilizer and the stabilizer is present in sufficient amounts to inhibit the fibrate crystallization.

The present invention includes fibrate formulations wherein the weight ratio of the fibrate to the stabilizer is about 50:1 to about 1:10.

The present invention also includes oral self-emulsifying pharmaceutical formulations with improved bioavailability, when compared to a commercial available formulation, comprising a therapeutically effective amount of fenofibrate or a fenofibrate derivative, one or more non-ionic surfactant with an HLB value higher or equal to about 10, one or more non-ionic co-surfactant with a HLB value lower about 10, one or more ionic surfactants or combinations thereof and a fenofibrate solubilizer selected from N—$C_{1-4}$ alkyl derivative of 2-pyrrolidone, mono- or di- or poly-ethylene glycol monoethers, $C_{8-12}$ fatty acid mono- or di-esters of propylene glycol, or combinations thereof wherein the fibrate to fibrate solubilizer weight ratio is between about 1:1 and about 1:100, and optionally one or more stabilizers selected from fatty acids, fatty alcohols, alcohols, long chain fatty acid esters, long chain ethers, hydrophilic derivatives of fatty acids, polyvinylpyrrolidones, polyvinylethers, polyvinyl alcohols, hydrocarbons, hydrophobic polymers, moisture-absorbing polymers.

The present invention additionally includes an oral self-emulsifying pharmaceutical formulation with improved bioavailability comprising a therapeutically effective amount of the fenofibrate or a fenofibrate derivative, one or more ionic surfactants or one or more non-ionic surfactant with an HLB value between 10 and 19, one or more non-ionic co-surfactant with a HLB value between 2 and 6, or combinations thereof and a fibrate solubilizer selected from N—$C_{1-4}$ alkyl derivative of 2-pyrrolidone, mono- or di- or poly-ethylene glycol monoethers, $C_{8-12}$ fatty acid mono- or di-esters of propylene glycol, or combinations thereof and optionally one or more stabilizers selected from fatty acids, fatty alcohols, alcohols, long chain fatty acid esters, long chain ethers, hydrophilic derivatives of fatty acids, polyvinylpyrrolidones, polyvinylethers, polyvinyl alcohols, hydrocarbons, hydrophobic polymers, moisture-absorbing polymers, wherein the bioavailability of the active ingredient is significantly enhanced when compared to a commercial available formulation.

According to a further aspect of the invention, there is provided a method for treating a mammal with hypercholesterolaemia or hypertriglyceridaemia comprising the oral administration of a fibrate self-emulsifying formulation containing a therapeutically effective dose of fenofibrate or a fenofibrate derivative dissolved in N-alkyl derivative of 2-pyrrolidone, mono- and di- or poly-ethylene glycol monoethers, $C_{8-12}$ fatty acid mono- or di-esters of propylene glycol, or combinations thereof and at least one surfactant selected from nonionic, anionic, cationic, and zwitterionic surfactants and combinations thereof, and optionally one or more stabilizers selected from fatty acids, fatty alcohols, alcohols, long chain fatty acid esters, long chain ethers, hydrophilic derivatives of fatty acids, polyvinylpyrrolidones, polyvinylethers, polyvinyl alcohols, hydrocarbons, hydrophobic polymers, moisture-absorbing polymers.

The present invention includes self-emulsifying formulations described above wherein the absorption of fenofibrate in fasted patients is significantly ($P<0.05$) enhanced when compared to a commercial available formulation such as Lipanthyl® (trade mark of Groupe Fournier) or TriCor® (trade mark of Abbott Laboratories).

In an embodiment of the present invention fibrate formulations described above wherein the improvement in $C_{max}$ is at least 1.2 times than that for commercial formulation and/or the $AUC_{0-\infty}$ improvement is at least 1.5 times that of commercial formulation when dosed in the fasted state.

The scope of the invention includes a pharmaceutical dosage unit for oral administration comprising of a self-emulsifying fibrate formulation containing a therapeutically effective dose of fenofibrate or a fenofibrate derivative dissolved in a fibrate solubilizer containing N-alkyl derivative of 2-pyrrolidone, mono- or di- or poly-ethylene glycol monoethers, $C_{8-12}$ fatty acid mono- or di-esters of propylene glycol, or combinations thereof and at least one surfactant selected from nonionic, anionic, cationic, and zwitterionic surfactants or combinations thereof wherein the fibrate to fibrate solubilizer weight ratio is between about 1:1 and about 1:100, and optionally one or more stabilizers selected from fatty acids, fatty alcohols, alcohols, long chain fatty acid esters, long chain ethers, hydrophilic derivatives of fatty acids, polyvinylpyrrolidones, polyvinylethers, polyvinyl alcohols, hydrocarbons, hydrophobic polymers, moisture-absorbing polymers, and the absorption of the fibrate in fasted mammals is significantly ($P<0.05$) enhanced when compared to a commercial available formulation such as Lipanthyl® (trade mark of Groupe Fournier) or TriCor® (trade mark of Abbott Laboratories). The present invention includes formulations wherein the concentration of the fibrate is above the saturation point of the selected fibrate solubilizer and the stabilizer is present in sufficient amounts to inhibit the fibrate crystallization.

DETAILED DESCRIPTION OF THE INVENTION

The present invention provides non-aqueous self-emulsifying formulations with enhanced systemic absorption of fenofibrate and/or derivatives of fenofibrate in both fed and fasted patients when compared to a commercial available formulation.

Due to the physicochemical properties of fibrates such as fenofibrate, the systemic absorption of the drug is believed to be dissolution rate limited. The present invention provides an oral self-emulsifying formulation wherein the fenofibrate or fenofibrate derivative is dissolved in fibrate solubilizer containing a solvent such as the N-alkyl derivatives of 2-pyrrolidone, mono- or di- or polyethylene glycol monoethers, $C_{8-12}$ fatty acid mono or di-esters of propylene glycol or glycerol, or combinations thereof. Additionally the formulation object of the present invention contains a surfactant that may be ionic or non-ionic or a combination of both. The fibrate solubilizer used in the present invention additionally may act as an agent that prevents or minimizes the crystallization of fibrate. The fibrate solubilizer may be a complexing agent soluble in water. With the complete dissolution of the fibrate, the fibrate solution allows for an increase in absorption of the fibrate by the patient. The ease with which the fenofibrate or fenofibrate derivative dissolves in a solvent is inversely proportional to the particle size of the fibrate.

Therefore, the present invention includes an oral self-emulsifying fibrate formulation comprising fenofibrate or a fenofibrate derivative and a solubilizer that allows the complete dissolution of the fenofibrate or a fenofibrate derivative and prevents or minimizes the crystallization of fibrate in the formulation. The present invention includes fibrate self-emulsifying formulation wherein the fibrate to fibrate solubilizer weight ratio is between about 1:1 and about 1:100.

The fibrate solubilizer may comprise one or more solvents (e.g. N-methyl-2-pyrrolidone, diethylene glycol monoether, $C_{8-12}$ fatty acid mono or di-esters of propylene glycol or glycerol), surfactants (ionic or non-ionic), optional co-surfactants, and stabilizing agents or stabilizers. Stabilizers that may be used in formulations object of the present invention are agents that will (1) improve the compatibility of excipients with the encapsulating materials such as gelatin, (2) improve the physical (e.g. prevent crystal growth of fenofibrate) and chemical stability of fenofibrate and/or fibrate derivatives, and/or (3) improve formulation stability. Stabilizers may be selected from fatty acids, fatty alcohols, alcohols, long chain fatty acid esters, long chain ethers, hydrophilic derivatives of fatty acids, polyvinylpyrrolidones, polyvinylethers, polyvinyl alcohols, hydrocarbons, hydrophobic polymers, moisture-absorbing polymers, and combinations thereof. Amide analogues of the above stabilizers can also be used. The chosen stabilizer may change the hydrophobicity of the formulation (e.g. oleic acid, waxes), or improve the mixing of various components in the formulation (e.g. ethanol), control the moisture level in the formula (e.g. PVP), control the mobility of the phase (substances with melting points higher than room temperature such as long chain fatty acids, alcohols, esters, ethers, amides etc. or mixtures thereof; waxes), and/or improve the compatibility of the formula with encapsulating materials (e.g. oleic acid or wax). Some of these stabilizers may be used as solvents/co-solvents (e.g. ethanol). Stabilizers may be present in sufficient amount to inhibit the fibrate crystallization, especially in formulations wherein the concentration of the fibrate is above the saturation point of N-alkyl derivative of 2-pyrrolidone, mono- or di- or poly-ethylene glycol monoethers, C8–12 fatty acid mono- or di-esters of propylene glycol.

Examples of stabilizers include, but are not limited to, saturated, monoenoic, polyenoic, branched, ring-containing, acetylenic, dicarboxylic and functional-group-containing fatty acids such as oleic acid, caprylic acid, capric acid, caproic acid, lauric acid, myristic acid, palmitic acid, stearic acid, behenic acid, linoleic acid, linolenic acid, EPA, DHA; fatty alcohols such as stearyl alcohol, cetyl alcohol, ceteryl alcohol; other alcohols such as ethanol, isopropyl alcohol, butanol; long chain fatty acid esters, ethers or amides such as glyceryl stearate, cetyl stearate, oleyl ethers, stearyl ethers, cetyl ethers, oleyl amides, stearyl amides; hydrophilic derivatives of fatty acids such as polyglyceryl fatty acids, polyethylene glycol fatty acid esters; PVPs, PVAs, waxes etc.

In an embodiment of the present invention the fibrate solubilizer may be selected from solvents such as alcohols, propylene glycol, polyethylene glycol, N-alkyl derivative of 2-pyrrolidone, mono- or di- or poly-ethylene glycol monoethers, propylene glycol mono- or di-esters, medium chain mono-, di-glycerides, or mixtures thereof. The present invention includes self-emulsifying fibrate formulation wherein the fibrate to fibrate solubilizer weight ratio is between about 1:1 and about 1:100.

A high load oral self-emulsifying pharmaceutical formulation with improved bioavailability comprising a therapeutically effective amount of fenofibrate, a fenofibrate derivative or mixtures thereof dissolved in a fibrate solubilizer comprising a solvent selected from N-alkyl derivatives of 2-pyrrolidone, mono- or di- or poly-ethylene glycol monoethers, $C_{8-12}$ fatty acid mono or di-esters of propylene glycol, or combinations thereof, a stabilizer in sufficient amount to prevent crystal growth of the fibrate wherein fibrate remains in solution and no crystallization of fibrate is observed for at least 24 hours, and a surfactant, wherein the fenofibrate concentration is close to or greater than the saturation point concentration at room temperature of the chosen solvents. The present invention includes formulations wherein the saturation factor is between about 1.05 and 2.5, wherein the saturation factor is defined as the ratio of the amount of the fibrate in the formulation to the sum of maximum fibrate solubility in each excipient fractions.

The present invention includes fibrate formulations wherein the weight ratio of the fibrate to the stabilizer is about 50:1 to about 1:10. A fibrate to stabilizer ratio of about 1:1 is included in the invention. A fibrate to stabilizer ratio of about 2:1 is also included in the present invention.

As used in this application, the term "fatty acid" represents a $C_{1-30}$ unbranched or branched, saturated or unsaturated hydrocarbon chain and one or more terminal carboxyl groups. The fatty acids may additionally have other functional groups or substituents attached.

The term "HLB" value is defined as hydrophilic-lipophilic balance and defines the relative hydrophilicity and hydrophobicity of the surfactant. Surfactants with lower HLB values are more hydrophobic, and have greater solubility in oils, while surfactants with higher HLB values are more hydrophilic, and have greater solubility in aqueous solutions. Surfactants having an HLB value less than about 10 are considered to be hydrophobic surfactants. Therefore hydrophilic surfactants have HLB values greater than about 10. Combinations of hydrophilic surfactants and hydrophobic surfactants thereof are within the scope of the present invention.

The term "self-emulsifying" formulation used herein refers to a concentrated composition capable of generating an emulsion or microemulsion upon mixing with an aqueous media.

The term "fenofibrate" is a fibrate and is defined as a compound of formula (I), 2-[4-(4-Chlorobenzoyl)phenoxy]-2-methylpropanoic acid 1-methylethyl ester:

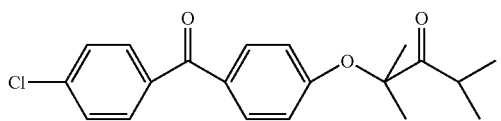

(I)

The term "fenofibrate derivatives" is defined as a compound of formula (II)

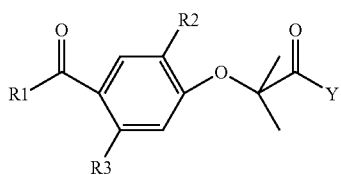

(II)

wherein $R_1$ represents a phenyl group or a phenyl group substituted by one or more $CH_3$, $CF_3$ or by halogens;

$R_2$ and $R_3$ independently represent a hydrogen atom or a halogen atom (preferably fluorine, chlorine, or bromine), an $C_{1-4}$ alkyl or an $C_{1-5}$ alkoxy or one of the following groups: $CF_3$, $SCH_3$, $SOCH_3$, $SO_2CH_3$, or OH; and Y represents one of the following groups: OH; $C_{1-5}$ alkoxy, preferably in $C_1$–$C_4$; —$NR_4R_5$; —$NHCH_2CH_2NR_4R_5$; or —O—$C_{1-6}$ alkylene-$NR_4R_5$, with the alkylene having, in particular, two to six atoms of carbon, and with $R_4$ and $R_5$ being identical or different and each representing a hydrogen atom or one of the following groups: $C_{1-5}$ alkyl, $C_3$–$C_7$ cycloalkyl, preferably $C_{5-6}$ cycloalkyl; $C_{6-10}$ aryl or aryl substituted on the aromatic residue by one or more halogen, methyl, or —$CF_3$ groups; or else $R_4$ and $R_5$ constitute, together with the nitrogen atom to which they are connected, one of the following groups: either an n-heterocyclic group having 5 to 7 vertices capable of enclosing a second heteroatom selected from N, O, and S, and capable of being substituted; or else an amide residue derived from lysine or cysteine; including the pharmaceutically acceptable salts, esters, amides and prodrugs thereof wherein said derivative has a solubility not less than 0.5 mg/ml in the solubilizers used in the fibrate formulation object of the present invention.

As used in the present disclosure, the term "mono- or di- or poly-ethylene glycol monoethers" includes diethylene glycol monoethers and ethyleneglycol monoethers as well as other higher-ethylene glycol monoethers.

In a further embodiment of the present invention an oral self-emulsifying fenofibrate formulation comprising fenofibrate or a fenofibrate derivative and a fibrate solubilizer is N-alkyl derivative of 2-pyrrolidone, mono- or di- or poly-ethylene glycol monoethers, $C_{8-12}$ fatty acid mono or di-esters of propylene glycol, or combinations thereof and one or more surfactants is provided. The formulations described may further contain a gelling agent that alters the texture of the final formulation through formation of a gel.

Gelling agents used in the present invention include but are not limited to carrageenan, cellulose gel, colloidal silicon dioxide, gelatin, propylene carbonate, carbonic acid, alginic acid, agar, carboxyvinyl polymers or carbomers and polyacrylamides, acacia, ester gum, guar gum, gum arabic, ghatti, gum karaya, tragacanth, terra, pectin, tamarind seed, larch arabinogalactan, alginates, locust bean, xanthan gum, starch, veegum, tragacanth, polyvinyl alcohol, gellan gum, hydrocolloid blends, and povidone.

The present invention further includes an oral self-emulsifying fibrate formulation with improved oral bioavailability comprising a therapeutically effective amount of the fenofibrate or fenofibrate derivative dissolved in a fibrate solubilizer selected from N—$C_{1-4}$ alkyl derivative of 2-pyrrolidone, mono- or di- or poly-ethylene glycol monoethers, $C_{8-12}$ fatty acid mono or di-esters of propylene glycol, or combinations thereof; and at least one surfactant selected from nonionic, anionic, cationic, and zwitterionic surfactants and combinations thereof. The surfactants selected can be one or more non-ionic surfactant with an HLB value higher or equal to about 10, one or more non-ionic co-surfactant with a HLB value lower about 10, one or more ionic surfactants or combinations thereof The present invention also provides an oral self-emulsifying formulation wherein the fenofibrate is dissolved in a fibrate solubilizer selected from N—$C_{1-4}$ alkyl derivative of 2-pyrrolidone, mono- or di- or polyethylene glycol monoethers, $C_{8-12}$ fatty acid mono- or di-esters of propylene glycol, or combinations thereof and one or more non-ionic surfactant with an HLB value higher or equal to about 10, one or more non-ionic co-surfactant with a HLB value lower or equal to about 6, or an ionic surfactant or combinations thereof wherein the resulting fenofibrate self-emulsifying formulation allows for an improved systemic absorption of the fenofibrate by the patient.

The present invention further provides an oral self-emulsifying formulation wherein the fenofibrate is dissolved in a solubilizer selected from N—$C_{1-4}$ alkyl derivative of 2-pyrrolidone, mono- or di- or polyethylene glycol monoethers, $C_{8-12}$ fatty acid mono- or di-esters of propylene glycol, or combinations thereof and one or more non-ionic surfactant with an HLB value between 10 and 19, one or more non-ionic co-surfactant with a HLB value between 2 and 6, or an ionic surfactant or combinations thereof herein the resulting fenofibrate self-emulsifying formulation allows for an improved systemic absorption of the fenofibrate by the patient.

The present invention includes an oral self-emulsifying pharmaceutical formulation with improved bioavailability comprising a therapeutically effective amount of the fenofibrate, a fenofibrate derivative or mixtures thereof and one or more N-alkyl derivative of 2-pyrrolidone, mono- or di- or poly-ethylene glycol monoethers or mixtures thereof, combined with at least one $C_{8-12}$ fatty acid mono and di-esters of polyethylene glycol or mixtures of $C_{8-12}$ fatty acid mono and di-esters of polyethylene glycol and fatty acids, and at least one surfactant with an HLB value higher than about 10 and at least one co-surfactants with an HLB value lower than or equal to about 6. The invention includes formulations wherein the combinations of the high HLB and low HLB value surfactants have a final HLB value equal to or lower than 10. Optionally the formulation may also contain a stabilizer The surfactants used in the present invention include nonionic, anionic, cationic, and zwitterionic surfactants and combinations thereof. These surfactants may include non-ionic surfactants such as fatty acid esters or amides or ether analogues, or hydrophilic derivatives thereof. Monoesters or diesters, or hydrophilic derivatives thereof; or mixtures thereof. Monoglycerides or diglycerides, or hydrophilic derivatives thereof; or mixtures thereof. Mixtures having enriched mono- or/and diglycerides, or hydrophilic derivatives thereof; maybe partially derivatized with a hydrophilic moiety; Monoesters or diesters or multiple-esters of other alcohols, polyols, saccharides or oligosaccharides or polysaccharides, oxyalkylene oligomers or polymers or block polymers; or hydrophilic derivatives thereof; the amide analogues thereof. Fatty acid derivatives of amines, polyamines, polyimines, aminoalcohols, aminosugars, hydroxyalkylamines, hydroxypolyimines, peptides, polypeptides; the ether analogues thereof. Surfactants can also be ionic or zwitterionic surfactants such as fatty acid salts, bile salts, sulfates, sulfonates, sulfosuccinates, carboxylates, lactylates, phospholipids and derivatives, quaternary ammonium salts, amine salts, polyethoxylated ammonium salts, or mixtures thereof.

The present invention includes the use of surfactants selected from sodium lauryl sulfate, sodium taurocholate, lecithin, lyso-lecithin, phosphatidyl glycerol, polyethylene glycol-phosphatidyl ethanolamine, cetyl trimethyl ammonium bromide, lauryl betaine, sucrose esters, polysorbates, sorbitan fatty acid esters, polyethylene glycosylated glycerides, PEGylated glycerides and combinations thereof. These non-ionic surfactant may include mixtures of monoglycerides, diglycerides, and triglycerides and monoesters and diesters of polyethylene glycol, polyethylene glycosylated almond glycerides, polyethylene glycosylated corn glycerides, polyethylene glycosylated caprylic/capric triglyceride, polysorbate 20, polysorbate 60, polysorbate 80, Polyoxyl 20 Cetostearyl Ether, Polyoxyl 10 Oleyl Ether and combinations thereof. Additionally suitable non-ionic surfactants include PEG stearate, PEG hydrogenated castor oil, PEG laurate, PEG apricot kernel oil esters, PEG caprylate, PEG caprate, PEG myristate, PEG palmitate, and PEG oleate and combinations thereof.

Examples of the surfactants include, but are not limited to, medium chain transesterification products of oils and alcohols, monoglycerides or diglycerides or mixtures thereof, polyethylene glycol fatty acid monoesters or diesters or mixtures thereof, polyethylene glycol sorbitan fatty acid esters, polyethylene glycol alkyl ethers, propylene glycol fatty acid monoesters or diesters or mixtures thereof, POE-POP block copolymer fatty acid monoesters or diesters or mixtures thereof, sugar esters, bile salts, fatty acid salts, bisalkyl sulfosuccinate salts, phospholipids, hydrophilic derivatives of phospholipids, fatty acid derivatives of polyamines or polyimines or aminoalcohols or aminosugars or peptides or polypeptides; or mixtures the above surfactants thereof.

The following specific examples of surfactants are for demonstration purpose and in no way they serve as any limitations on the scope of the surfactants: PEG-8 caprylic/capric glycerides (Labrasol, Acconon MC-8), PEG-6 caprylic/capric glycerides (Softgen 767, Acconon CC-6), PEG-12 caprylic/capric glycerides (Acconon CC-1 2), PEG-35 castor oil (Cremophor EL), PEG-60 corn glycerides (Crovol M70), PEG-23 lauryl ether (Brij 35), PEG-8 laurate (MAPEG 400 ML), CTAB, DODAB, sodium bis(2-ethylhexyl) sulfosuccinate, glyceryl fatty acids, glyceryl fatty acid esters, propylene glycol laureate, glyceryl glycol esters, polyglycolyzed glycerides, propylene glycol esters or partial esters and polyoxyethyl steryl ethers, or combinations thereof.

Surfactants can be used in combination with other surfactants as co-surfactants. Suitable co-surfactants include surfactants selected from the above list having a HLB lower than 10.

Surfactants used in the oral self-emulsifying pharmaceutical formulation with improved bioavailability object of the present invention may include phospholipids, sorbitan tristearate, sorbitan sesquioleate, glyceryl monostearate, sorbitan monooleate, sorbitan monostearate, sorbitan distearate, propylene glycol monostearate, glyceryl monooleate, glyceryl stearate mono, propylene glycol monolaurate, glyceryl monolaurate, diethylene glycol monoethyl ether and combinations thereof.

The scope of the present invention includes formulations summarized in Tables 1.

TABLE 1

Quantitative representation of self-emulsifying formulations providing for enhanced systemic absorption of fenofibrate

| Ingredient | Amount (% w/w) |
| --- | --- |
| Fenofibrate | 5–40 |
| Solubilizers | 20–80 |
| Surfactant | 2–25 |
| Stabilizers and other possible formulation additives* | 0–30 |

*Excipients required for stability enhancement of the final formulation, antioxidants, preservatives, thickening agents, suspending agents, buffering agents, or other suitable additives known in the art.

The present invention includes a fenofibrate formulation wherein the fibrate solubilizer includes the use of N-alkyl derivatives 2-pyrrolidones, wherein the alkyl group has 1 to 4 carbons, mono- or di- or poly-ethylene glycol monoethers, $C_{8-12}$ fatty acid mono or di-esters of propylene glycol, or combinations thereof is provided. The present invention includes N-alkyl derivatives 2-pyrrolidone wherein the alkyl group has 1 to 3 carbons.

The amount of fibrates such as fenofibrate, fenofibrate derivatives or mixtures thereof contained in the formulation of this invention is not specifically restricted but may be any amount convenient for pharmaceutical purposes. A concentrated solution close to or greater than the saturation point of the fibrate in solvents such as the N-alkyl derivatives of 2-pyrrolidone, mono- or di- or poly-ethylene glycol monoethers, $C_{8-12}$ fatty acid mono or di-esters of propylene glycol, or combinations thereof are included in the scope of the present invention. If the fibrate concentration desired in the formulation is higher that the saturation point in the chosen solvent, one or more stabilizers are added to obtain a fibrate solution that would prevent crystal growth in supersaturated fibrate for at least 24 hours. For example the solubility of fenofibrate in N-methyl-2-pyrrolidone, mono- or di- or poly-ethylene glycol monoethers, $C_{8-12}$ fatty acid mono or di-esters of propylene glycol can be determined and the solubility of fenofibrate in each individual solvents or a combination of solvents can be calculated based the fraction and individual solubility. So a concentrated fenofibrate solutions of greater than or equal to the calculated solubility of fenofibrate would be of interest for use in the oral formulation object of the present invention and would require the use of one or more stabilizers in a sufficient amount to prevent the crystal growth of fenofibrate in the fibrate solution. The present invention would also include the use of fenofibrate in the above-mentioned solvent solutions with concentrations below or equal to the saturation point with or without the use of a stabilizer.

The present invention includes formulation wherein the fibrate concentration is between 20 and 500 mg/ml of formulation. Fibrate concentrations between 50 and 300 mg/ml of formulation are included in the scope of the present invention. The total amount of fibrates such as fenofibrate, fenofibrate derivatives or mixtures thereof in formulations in the present invention is between about 5% to about 40% by weight.

In an alternate embodiment of the present invention, one or more of the fenofibrate or fenofibrate derivative solubilizers are selected from N-methyl-2-pyrrolidone, N-ethyl-2-pyrrolidone, N-propyl-2-pyrrolidone, N-isopropyl-2-pyrrolidone, N-butyl-2-pyrrolidone, N-2-hydroxyethyl)-2-pyrrolidone, diethylene glycol monoethyl ether, diethylene glycol monobutyl ether, ethylene glycol monoethyl ether, ethylene glycol monobutyl ether, tri- or tetra-ethylene glycol monoethyl ether, $C_{8-12}$ fatty acid mono-esters of propylene glycol, $C_{8-12}$ fatty acid di-esters of propylene glycol and combinations thereof. The invention includes the combinations of the N-alkyl derivatives of 2-pyrrolidone with mono- or di- or poly-ethylene glycol monoethers, $C_{8-12}$ fatty acid mono or di-esters of propylene glycol. The formulation object of the present invention may use N-methyl-2-pyrrolidone, diethylene glycol monoethyl ether, propylene glycol mono- or diesters of caprylic acid, capric acid, lauric acid or other medium chain fatty acids or fatty acid mixtures, and combinations thereof as solubilizers of fenofibrate. The $C_{8-12}$ fatty acid mono- and diesters of propylene glycol and combinations thereof also include use of Captex® 100, Captex® 200, Captex® 800, Captex®200 E-6, Capmul® PG-8, Capmul® PG-12, (Abitec Corp.), Miglyol 840, Imwitor 408, Imwitor 412 (SASOL), NEOBEE M-20 (Stepan) TRIOL PR-91, MYRITOL PC and other commercially available products that belong to the category of materials described. Combinations of N-Methyl-2-Pyrrolidone and diethylene glycol monoethyl ether as fibrate solubilizers are within the scope of the present invention. Combinations of $C_{8-12}$ fatty acid mono-esters and di-esters of propylene glycol are also within the scope of the present invention. Combinations of mono- and/or di- and/or poly-ethylene glycol monoethers with $C_{8-12}$ fatty acid mono-esters and/or di-esters of propylene glycol are within the scope of the current invention. The invention includes combinations of N-methyl-2-pyrrolidone and diethylene glycol monoethyl ether wherein the weight ratios of N-methyl-2-pyrrolidone to diethylene glycol monoethyl ether is between about 100:1 and about 1:100. The invention also includes combinations of N-methyl-2-pyrrolidone and diethylene glycol monoethyl ether wherein the weight rations of N-methyl-2-pyrrolidone to diethylene glycol monoethyl ether is between about 10:1 and about 1:10.

In a further embodiment of the present invention, the fibrate solubilizer is chosen from combinations of N—$C_{1-4}$ alkyl derivative of 2-pyrrolidone or a mono- or di- or poly-ethylene glycol monoethers, one or more $C_{8-12}$ fatty acid mono or di-esters of propylene glycol, or combinations thereof. The weight ratio of the N—$C_{1-4}$ alkyl derivative of 2-pyrrolidone or a mono- or di- or polyethylene glycol monoethers or combinations thereof to one or more $C_{8-12}$ fatty acid mono or di-esters of propylene glycol is between about 100:1 to about 1:100. The present invention includes ratios between 10:1 to about 1:50.

The present invention also includes combinations of mono- and/or di- and/or poly-ethylene glycol monoethers with $C_{8-12}$ fatty acid mono-esters and/or di-esters of propylene glycol wherein the ratios of monoethers to esters of propylene glycol is between about 100:1 to about 1:100. The invention further includes combinations of $C_{8-12}$ fatty acid mono-esters and di-esters of propylene glycol wherein the ratios of mono-esters to di-esters is between about 100:1 to about 1:100. Propylene glycol diesters of mixed $C_{8-12}$ fatty acids are also within the scope of the present invention.

The amount of fibrate solubilizer used will depend on the dose of fibrate. In one of the embodiments of the present invention, enough solubilizer should be used to maintain the fibrate in solution. The weight ratio of fibrate to the fibrate solubilizer is chosen so as to obtain a complete dissolution of fenofibrate or fenofibrate derivatives. The fibrate:fibrate solubilizer ratio is chosen to obtain a solution wherein fibrate remains in solution and no crystallization is observed for at least 24 hours. The weight ratio of fibrate to fibrate solubilizer may be between about 1:1 to about 1:100. The weight ratios include about 1:1 to about 1:10. The fibrate: fibrate solubilizer weight ratio may also be between about 1:2 to about 1:100. The fibrate:fibrate solubilizer weight ratio between about 3:4 to about 1:10 is within the scope of the invention. The total amount of solubilizers in formulations of the present invention is between about 20% to about 80% by weight.

The formulations object of the present invention may use a solubilizers of fenofibrate selected from N-methyl-2-pyrrolidone, diethylene glycol monoethyl ether, propylene glycol mono- or diesters of caprylic acid, capric acid, lauric acid or other medium chain fatty acids or fatty acid mixtures, and combinations thereof.

The amount of solubilizers required to obtain a complete dissolution of fenofibrate or fenofibrate derivatives can be reduced by use of stabilizers. The fibrate solubilizers comprising N-alkyl derivatives of 2-pyrrolidone, mono- or di- or poly-ethylene glycol monoethers, $C_{8-12}$ fatty acid mono- or di-esters of propylene glycol or combinations there of can be used in conjunction with one or more stabilizers selected from fatty acids, fatty alcohols, alcohols, long chain fatty acid esters, long chain ethers, hydrophilic derivatives of fatty acids, polyvinylpyrrolidones, polyvinylethers, polyvinyl alcohols, hydrocarbons, hydrophobic polymers, moisture-absorbing polymers. The stabilizer is present in sufficient amounts to inhibit the fibrate crystallization. The formulations object of the present invention may use a solubilizer of fenofibrate selected from N-methyl-2-pyrrolidone, diethylene glycol monoethyl ether, propylene glycol mono- or diesters of caprylic acid, capric acid, lauric acid or other medium chain fatty acids or fatty acid mixtures, and combinations thereof.

The present invention includes a pharmaceutical dosage unit for oral administration comprising of a self-emulsifying fibrate formulation containing a therapeutically effective dose of fenofibrate or a fenofibrate derivative dissolved in a fibrate solubilizer containing N-alkyl derivative of 2-pyrrolidone, mono- or di-ethylene glycol monoethers, $C_{8-12}$ fatty acid mono- or di-esters of propylene glycol, or combinations thereof and at least one surfactant selected from nonionic, anionic, cationic, and zwitterionic surfactants or combinations thereof wherein the fibrate to fibrate solubilizer weight ratio is between about 1:1 and about 1:100, and optionally one or more stabilizers selected from fatty acids, fatty alcohols, alcohols, long chain fatty acid esters, long chain ethers, hydrophilic derivatives of fatty acids, polyvinylpyrrolidones, polyvinylethers, polyvinyl alcohols, hydrocarbons, hydrophobic polymers, moisture-absorbing polymers. It optionally further Incudes other possible formulation additives including excipients required for stability enhancement of the final formulation, antioxidants, preservatives, thickening agents, suspending agents, buffering agents, or other suitable additives known in the art. The total amount of stabilizers and other possible formulation additives is between about 0% to about 30% by weight.

The % bioavailability enhancement value is defined as the ratio obtained by formula (III):

$$\{(AUC_{0\text{-}24 \ (fibrate \ formulation)}/Dose_{fibrate \ formulation})/ (AUC_{0\text{-}24 \ (Commercial \ formulation)}/ Dose_{Commercial \ formulation})\} \times 100 \quad (III)$$

The present invention includes an oral self-emulsifying pharmaceutical formulation with improved oral bioavailability comprising a therapeutically effective amount of fenofibrate, a fenofibrate derivative or mixtures thereof in one or more fibrate solubilizers selected from N-alkyl derivative of 2-pyrrolidone, mono- or di- or poly-ethylene glycol monoethers, $C_{8\text{-}12}$ fatty acid mono- or di-esters of propylene glycol, or combinations thereof; and at least one surfactant wherein the bioavailability of said formulation is significantly (P<0.05) enhanced in both the rate and the extent ($C_{max}$ and $AUC_{0\text{-}\infty}$) of absorption as compared to that of a commercial formulation. The present invention includes said formulations wherein the improvement in $C_{max}$ is at least about 1.2 times that of a commercial formulation such as Lipanthyl® (trade mark of Groupe Fournier) or TriCor® (trade mark of Abbott Laboratories) and/or the $AUC_{0\text{-}\infty}$ improvement is at least about 1.5 times that of a commercial formulation such as. Lipanthyl® (trade mark of Groupe Fournier) or TriCor® (trade mark of Abbott Laboratories) when dosed in the fasted state. The present invention includes formulations wherein the $AUC_{0\text{-}\infty}$ improvement is between about 1.5 times and about 5 times that of a commercial formulation such as Lipanthyl® (trade mark of Groupe Fournier) or TriCor® (trade mark of Abbott Laboratories) when dosed in the fasted state.

The present invention further includes an oral self-emulsifying fibrate formulation with improved oral bioavailability comprising a therapeutically effective amount of the fenofibrate or fenofibrate derivative dissolved in one or more fibrate solubilizers selected from N—$C_{1\text{-}4}$ alkyl derivative of 2-pyrrolidone, mono- or di- or poly-ethylene glycol monoethers, $C_{8\text{-}12}$ fatty acid mono- or di-esters of propylene glycol, or combinations thereof and at least one surfactant selected from non-ionic surfactants with a high HLB value lower than or equal to 10, ionic surfactants or combinations thereof wherein weight ratio of fibrate to fibrate solubilizer is between about 1:1 to about 1:100 and the oral bioavailability of said formulation is significantly (P<0.05) enhanced in both the rate and the extent ($C_{max}$ and $AUC_{0\text{-}\infty}$) of absorption as compared to that of a commercial formulation such as Lipanthyl® (trade mark of Groupe Fournier) or TriCor® (trade mark of Abbott Laboratories). The present invention includes said formulations wherein the improvement in $C_{max}$ is at least 1.2 times that of a commercial formulation such as Lipanthyl® (trade mark of Groupe Fournier) or TriCor® (trade mark of Abbott Laboratories) and/or the $AUC_{0\text{-}\infty}$ improvement is at least 1.5 times that of a commercial formulation such as Lipanthyl® (trade mark of Groupe Fournier) or TriCor® (trade mark of Abbott Laboratories) when dosed in the fasted state. The present invention includes formulations wherein the $AUC_{0\text{-}\infty}$ improvement is between about 1.5 times and about 5 times that of a commercial formulation such as Lipanthyl® (trade mark of Groupe Fournier) or TriCor® (trade mark of Abbott Laboratories) when dosed in the fasted state.

The present invention also provides an oral self-emulsifying formulation wherein the fenofibrate is dissolved in one or more fibrate solubilizers selected from N—$C_{1\text{-}4}$ alkyl derivative of 2-pyrrolidone, mono- or di- or poly-ethylene glycol monoethers, $C_{8\text{-}12}$ fatty acid mono- or di-esters of propylene glycol, or combinations thereof, and one or more surfactants selected from ionic surfactants, non-ionic surfactants with an HLB value higher or equal to about 10 in combination with one or more non-ionic co-surfactant with a HLB value lower about 10, wherein the weight ratio of fenofibrate to fibrate solubilizer may be between about 1:1 to about 1:100 and the resulting fenofibrate self-emulsifying formulation allows for an improved systemic absorption of the fenofibrate by the patient and the oral bioavailability of said formulation is significantly (P<0.05) enhanced in both the rate and the extent ($C_{max}$ and $AUC_{0\text{-}\infty}$) of absorption as compared to that of a commercial formulation such as Lipanthyl® (trade mark of Groupe Fournier) or TriCor® (trade mark of Abbott Laboratories). The present invention includes said formulations wherein the improvement in $C_{max}$ is at least 1.2 times that a commercial formulation such as Lipanthyl® (trade mark of Groupe Fournier) or TriCor® (trade mark of Abbott Laboratories). and/or the $AUC_{0\text{-}\infty}$ improvement is at least 1.5 times that of a commercial formulation such as Lipanthyl® (trade mark of Groupe Fournier) or TriCor® (trade mark of Abbott Laboratories) when dosed in the fasted state. The present invention includes formulations wherein the $AUC_{0\text{-}\infty}$ improvement is between about 1.5 times and about 5 times that of a commercial formulation such as Lipanthyl® (trade mark of Groupe Fournier) or TriCor® (trade mark of Abbott Laboratories) when dosed in the fasted state.

The present invention additionally includes an oral self-emulsifying pharmaceutical formulation with improved bioavailability comprising a therapeutically effective amount of the fenofibrate or a fenofibrate derivative, a surfactant selected from ionic surfactants, non-ionic surfactants with an HLB value between 10 and 19 combined with one of more non-ionic co-surfactants with a HLB value between 2 and 6, and one or more fenofibrate solubilizers selected from N—$C_{1\text{-}4}$ alkyl derivative of 2-pyrrolidone, mono- or di- or poly-ethylene glycol monoethers, or $C_{8\text{-}12}$ fatty acid mono- or di-esters of propylene glycol, or combinations thereof wherein the bioavailability when compared to a commercial available formulation is enhanced due to a significantly (P<0.05) enhanced rate (reduction in the time $T_{max}$ to reach maximum plasma levels $C_{max}$) and/or extent of absorption ($AUC_{0\text{-}\infty}$).

The present invention further includes an oral self-emulsifying pharmaceutical formulation with improved oral bioavailability comprising a therapeutically effective amount of fenofibrate, a fenofibrate derivative or mixtures thereof in one or more fibrate solubilizers selected from N-alkyl derivative of 2-pyrrolidone, mono- or di- or poly-ethylene glycol monoethers, $C_{8\text{-}12}$ fatty acid mono- or di-esters of propylene glycol, or combinations thereof, one or more non-ionic or ionic surfactants or combinations thereof, and optionally one or more stabilizers selected from fatty acids, fatty alcohols, alcohols, long chain fatty acid esters, long chain ethers, hydrophilic derivatives of fatty acids, polyvinylpyrrolidones, polyvinylethers, polyvinyl alcohols, hydrocarbons, hydrophobic polymers and moisture-absorbing polymers, wherein the bioavailability of said formulation is significantly (P<0.05) enhanced in both the rate and the extent ($C_{max}$ and $AUC_{0\text{-}\infty}$) of absorption as compared to that of a commercial formulation. The present invention includes said formulations wherein the improvement in $C_{max}$ is at least about 1.2 times that of a commercial formulation such as Lipanthyl® (trade mark of Groupe Fournier) or TriCor® (trade mark of Abbott Laboratories) and/or the $AUC_{0-\infty}$ improvement is at least about 1.5 times that of a commercial formulation such as Lipanthyl® (trade mark of Groupe Fournier) or TriCor® (trade mark of Abbott Laboratories) when dosed in the fasted state. The present invention includes formulations wherein the $AUC_{0-\infty}$ improvement is between about 1.5 times and about 5 times that of a commercial formulation such as Lipanthyl (® (trade mark of Groupe Fournier) or TriCor® (trade mark of Abbott Laboratories) when dosed in the fasted state. The present invention includes formulations wherein the $AUC_{0-\infty}$ improvement is between about 1.5 times and about 5 times that of a commercial formulation such as Lipanthyl® (trade mark of Groupe Fournier) or TriCor® (trade mark of Abbott Laboratories) when dosed in the fasted state. The present invention includes formulations wherein the $C_{max}$ improvement is between about 1.2 times and about 5 times that of a commercial formulation such as Lipanthyl® (trade mark of Groupe Fournier) or TriCor® (trade mark of Abbott Laboratories) when dosed in the fasted state.

The present invention includes a pharmaceutical formulation with improved oral bioavailability in both fed and/or fasted patients when compared to a commercially available formulation comprising a therapeutically effective amount of the fenofibrate, a fenofibrate derivative or mixtures thereof dissolved in a solubilizer containing N-alkyl derivative of 2-pyrrolidone, mono- or di- or poly-ethylene glycol monoethers, or $C_{8-12}$ fatty acid mono- or di-esters of propylene glycol, or combinations thereof; and at least one surfactant wherein the fibrate to fibrate solubilizer weight ratio is between about 1:1 and about 1:100 and wherein the bioavailability is reflected by the improvement in $C_{max}$ is at least 1.2 times that a commercial formulation such as Lipanthyl® (trade mark of Groupe Fournier) or TriCor® (trade mark of Abbott Laboratories) and/or the $AUC_{0-\infty}$ improvement is at least 1.5 times that of a commercial formulation such as Lipanthyl® (trade mark of Groupe Fournier) or TriCor® (trade mark of Abbott Laboratories). The formulations object of the present invention may use a solubilizer of fenofibrate selected from N-methyl-2-pyrrolidone, diethylene glycol monoethyl ether, propylene glycol mono- or diesters of caprylic acid, capric acid, lauric acid or other medium chain fatty acids or fatty acid mixtures, and combinations thereof.

The present invention includes an oral self-emulsifying pharmaceutical formulation with improved bioavailability comprising a therapeutically effective amount of the fenofibrate, a fenofibrate derivative or mixtures thereof and dissolved in one or more solubilizers selected from N-alkyl derivative of 2-pyrrolidone, mono- or di- or poly-ethylene glycol monoethers, $C_{8-12}$ fatty acid mono- or di-esters of propylene glycol, or combinations thereof, and at least one surfactant selected from PEG-8 caprylic/capric glycerides (Labrasol, Acconon MC-8), PEG-6 caprylic/capric glycerides (Softgen 767, Acconon CC-6), PEG-12 caprylic/capric glycerides (Acconon CC-12), PEG-35 castor oil (Cremophor EL), PEG-60 corn glycerides (Crovol M70), PEG-23 lauryl ether (Brij 35), PEG-8 laurate (MAPEG 400 ML), phospholipids (lecithin), mono-acyl glycerides, sorbitan fatty acid esters (Span 20, Span 80 and the like), sucrose distearate, sodium lauryl sulfate, and combinations thereof. Optionally the formulation may include a stabilizer selected from fatty acids, fatty alcohols, alcohols, long chain fatty acid esters, long chain ethers, hydrophilic derivatives of fatty acids, polyvinylpyrrolidones, polyvinylethers, polyvinyl alcohols, hydrocarbons, hydrophobic polymers, moisture-absorbing polymers.

The present invention includes an oral self-emulsifying pharmaceutical formulation comprising a fibrate dissolved in a fibrate solubilizer composed selected from N-alkyl derivative of 2-pyrrolidone, mono- or di- or poly-ethylene glycol monoethers, $C_{8-12}$ fatty acid mono- or di-esters of propylene glycol, or combinations thereof; and at least one ionic or non-ionic surfactant or combinations thereof; and optionally one or more stabilizers wherein the fibrate is between about 5 W/W %, and about 40 W/W %, the fibrate solubilizer is between about 20 W/W % and about 80 W/W %; the surfactant is about 2 W/W %, and about 25 W/W %; and the stabilizer is between about 0 W/W % and about 30 W/W %.

The present invention also includes an oral self-emulsifying pharmaceutical formulation with improved bioavailability comprising a therapeutically effective amount of the fenofibrate, a fenofibrate derivative or mixtures thereof and one or more solubilizers selected from N-alkyl derivative of 2-pyrrolidone, mono- or di- or poly-ethylene glycol monoethers, $C_{8-12}$ fatty acid mono- or di-esters of polyethylene glycol, or combinations thereof, a surfactant selected from sodium lauryl sulfate, sodium taurocholate, lecithin, lysolecithin, phosphatidyl glycerol, polyethylene glycol-phosphatidyl ethanolamine, cetyl trimethyl ammonium bromide, lauryl betaine, bile salts, fatty acid salts, bisalkyl sulfosuccinate salts, sucrose esters, sorbitan fatty acid esters, polysorbates, poloxamers, polyethylene glycosylated glycerides, PEGylated glycerides and combinations thereof. These surfactants may include mixtures of monoglycerides, diglycerides, and triglycerides and monoesters and diesters of polyethylene glycol, polyethylene glycosylated almond glycerides, polyethylene glycosylated corn glycerides, polyethylene glycosylated caprylic/capric triglyceride, polysorbate 20, polysorbate 60, polysorbate 80, span 20, span 60, span 80, Polyoxyl 20 cetostearyl ether, polyoxyl 10 oleyl ether and combinations thereof. Additionally suitable non-ionic surfactants include PEG-fatty ethers, PEG-23 lauryl ether, PEG stearate, PEG hydrogenated castor oil, PEG laurate, PEG apricot kernel oil esters, PEG caprylate, PEG caprate, PEG myristate, PEG palmitate, and PEG oleate and other aforementioned surfactants and combinations thereof and optionally a stabilizer selected from fatty acids, fatty alcohols, alcohols, long chain fatty acid esters, long chain ethers, hydrophilic derivatives of fatty acids, polyvinylpyrrolidones, polyvinylethers, polyvinyl alcohols, hydrocarbons, hydrophobic polymers, moisture-absorbing polymers. The invention includes those oral self-emulsifying pharmaceutical formulation with improved bioavailability described above wherein the improvement in $C_{max}$ is at least 1.2 times that of a commercial formulation such as Lipanthyl® (trade mark of Groupe Fournier) or TriCor ® (trade mark of Abbott Laboratories) and/or the $AUC_{0-\infty}$ improvement is at least 1.5 times that of a commercial formulation such as Lipanthyl® (trade mark of Groupe Fournier) or TriCor® (trade mark of Abbott Laboratories) in fasted patients. The formulations object of the present invention may use as solubilizers of fenofibrate selected from N-ethyl-2-pyrrolidone, diethylene glycol monoethyl ether, propylene glycol mono- or diesters of caprylic acid, capric acid, lauric acid or other medium chain fatty acids or fatty acid mixtures, and combinations thereof.

All the formulations object of the present invention may be prepared using both micronized and non-micronized fibrate.

Other commonly used pharmaceutical excipients which may also be added to the formulations object of the present invention, these may include antioxidants, preservatives or stabilizing agents, such as butylated hydroxytoluene, butylated hydroxyanisole sodium bisulfide, sodium sulfite, citric acid, ascorbic acid, or EDTA, coloring agents and flavoring agents (to improve patient acceptance, especially for liquid dosage forms), and ingredients used to stabilize gelatin capsules, such as glycerine, or gelatin.

The fibrate formulations disclosed are useful in the treatment of hypercholesterolaemias and hypertriglyceridaemias in fed and fasted mammals, including humans. According to a further aspect of the invention, there is provided a method for treating a mammal with hypercholesterolaemia or hypertriglyceridaemia comprising the oral administration of an oral self-emulsifying formulation containing a therapeutically effective dose of fenofibrate or a fenofibrate derivative dissolved in N-alkyl derivative of 2-pyrrolidone, mono- or di- or poly-ethylene glycol monoethers, $C_{8-12}$ fatty acid mono- or di-esters of propylene glycol or combinations thereof and at least one surfactant selected from nonionic, anionic, cationic, and zwitterionic surfactants and combinations thereof, and optionally one or more stabilizers selected from fatty acids, fatty alcohols, alcohols, long chain fatty acid esters, long chain ethers, hydrophilic derivatives of fatty acids, polyvinylpyrrolidones, polyvinylethers, polyvinyl alcohols, hydrocarbons, hydrophobic polymers, moisture-absorbing polymers and mixtures thereof.

In an alternate embodiment of the present invention includes the use of an oral self-emulsifying formulation containing a therapeutically effective dose of fenofibrate or a fenofibrate derivative dissolved in N-alkyl derivative of 2-pyrrolidone, mono- or di- or poly-ethylene glycol monoethers, $C_{8-12}$ fatty acid mono- or di-esters of propylene glycol or combinations thereof and at least one surfactant selected from nonionic, anionic, cationic, and zwitterionic surfactants and combinations thereof, and optionally one or more stabilizers selected from fatty acids, fatty alcohols, alcohols, long chain fatty acid esters, long chain ethers, hydrophilic derivatives of fatty acids, polyvinylpyrrolidones, polyvinylethers, polyvinyl alcohols, hydrocarbons, hydrophobic polymers, moisture-absorbing polymers and mixtures thereof in the preparation of a medicament for the treatment of hypercholesterolaemias and hypertriglyceridaemias.

The present invention includes a solubilization process of fenofibrate, fenofibrate derivative or mixtures thereof wherein fenofibrate, fenofibrate derivative or combinations thereof are solubilized in N-alkyl derivative of 2-pyrrolidone or mixtures of N—$C_{1-4}$ alkyl derivative of 2-pyrrolidones or combinations of N—$C_{1-4}$ alkyl derivative of 2-pyrrolidone, mono- or di- or poly-ethylene glycol monoethers, $C_{8-12}$ fatty acid mono- or di-esters of propylene glycol or combinations thereof. The formulations object of the present invention may use a solubilizers of fenofibrate selected from N-methyl-2-pyrrolidone, diethylene glycol monoethyl ether, propylene glycol mono- or diesters of caprylic acid, capric acid, lauric acid or other medium chain fatty acids or fatty acid mixtures, and combinations thereof.

A further aspect of the present invention includes a process for improving the bioavailability of fenofibrate, a fenofibrate derivative or mixtures thereof comprising dissolving the active agent in a fibrate solubilizer selected from N-alkyl derivative of 2-pyrrolidone, mono- or di- or poly-ethylene glycol monoethers, $C_{8-12}$ fatty acid mono- or di-esters of polyethylene glycol, or mixtures thereof, and at least one surfactant selected from nonionic, anionic, cationic, and zwitterionic surfactants and combinations thereof; and optionally a stabilizer selected from fatty acids, fatty alcohols, alcohols, long chain fatty acid esters, long chain ethers, hydrophilic derivatives of fatty acids, polyvinylpyrrolidones, polyvinylethers, polyvinyl alcohols, hydrocarbons, hydrophobic polymers, moisture-absorbing polymers and mixtures thereof.

The oral formulation may be encapsulated in a hard or soft gelatin capsule, a starch capsule or any other pharmaceutically acceptable capsule.

The scope of the invention includes a pharmaceutical dosage unit for oral administration comprising a fibrate formulation containing a therapeutically effective dose of fenofibrate or a fenofibrate derivative dissolved in N-alkyl derivative of 2-pyrrolidone, mono- or di- or poly-ethylene glycol monoethers, $C_{8-12}$ fatty acid mono- or di-esters of propylene glycol or combinations thereof and at least one surfactant selected from nonionic, anionic, cationic, and zwitterionic surfactants and combinations thereof, and optionally one or more stabilizers selected from fatty acids, fatty alcohols, alcohols, long chain fatty acid esters, long chain ethers, hydrophilic derivatives of fatty acids, polyvinylpyrrolidones, polyvinylethers, polyvinyl alcohols, hydrocarbons, hydrophobic polymers, moisture-absorbing polymers and mixtures thereof.

The scope of the invention includes a pharmaceutical dosage unit for oral administration comprising a therapeutically effective amount of the fenofibrate, a fenofibrate derivative or mixtures thereof and one or more solubilizers selected from N-alkyl derivative of 2-pyrrolidone, mono- or di- or poly-ethylene glycol monoethers, $C_{8-12}$ fatty acid mono- or di-esters of polyethylene glycol, or combinations thereof, a surfactant selected from sodium lauryl sulfate, sodium taurocholate, lecithin, lyso-lecithin, phosphatidyl glycerol, polyethylene glycol-phosphatidyl ethanolamine, cetyl trimethyl ammonium bromide, lauryl betaine, bile salts, fatty acid salts, bisalkyl sulfosuccinate salts, sucrose esters, sorbitan fatty acid esters, polysorbates, poloxamers, polyethylene glycosylated glycerides, PEGylated glycerides and combinations thereof. These surfactants may include mixtures of monoglycerides, diglycerides, and triglycerides and monoesters and diesters of polyethylene glycol, polyethylene glycosylated almond glycerides, polyethylene glycosylated corn glycerides, polyethylene glycosylated caprylic/capric triglyceride, polysorbate 20, polysorbate 60, polysorbate 80, span 20, span 60, span 80, Polyoxyl 20 cetostearyl ether, polyoxyl 10 oleyl ether and combinations thereof. Additionally suitable non-ionic surfactants include PEG-fatty ethers, PEG-23 lauryl ether, PEG stearate, PEG hydrogenated castor oil, PEG laurate, PEG apricot kernel oil esters, PEG caprylate, PEG caprate, PEG myristate, PEG palmitate, and PEG oleate and other aforementioned surfactants and combinations thereof and optionally a stabilizer selected from fatty acids, fatty alcohols, alcohols, long chain fatty acid esters, long chain ethers, hydrophilic derivatives of fatty acids, polyvinylpyrrolidones, polyvinylethers, polyvinyl alcohols, hydrocarbons, hydrophobic polymers, moisture-absorbing polymers. The invention includes those oral self-emulsifying pharmaceutical formulation with improved bioavailability described above wherein the improvement in $C_{max}$ is at least 1.2 times that of a commercial formulation such as Lipanthyl® (trade mark of Groupe Fournier) or TriCor® (trade mark of Abbott Laboratories) and/or the $AUC_{0-\infty}$ improvement is at least 1.5 times that of a commercial formulation such as Lipanthyl® (trade mark of Groupe Fournier) or TriCor® (trade mark of Abbott Laboratories) in fasted patients. The present invention includes methods wherein the $AUC_{0-\infty}$ improvement is between about 1.5 times and about 5 times that of a commercial formulation such as Lipanthyl® (trade mark of Groupe Fournier) or TriCor® (trade mark of Abbott Laboratories) when dosed in the fasted state. The method object of the present invention may use a solubilizers of fenofibrate selected from N-methyl-2-pyrrolidone, diethylene glycol monoethyl ether, propylene glycol mono- or diesters of caprylic acid, capric acid, lauric acid or other medium chain fatty acids or fatty acid mixtures, and combinations thereof.

In an alternate embodiment of the present invention a method of preparation for a oral formulation of fenofibrate or fenofibrate derivative with an improved bioavailability comprising:

dissolving the fenofibrate, fenofibrate derivative or mixtures thereof in an appropriate volume of solubilizer selected from N-alkyl derivative of 2-pyrrolidone, mono- or di- or poly-ethylene glycol monoethers, $C_{8-12}$ fatty acid mono- or di-esters of propylene glycol or combinations thereof to obtain a fenofibrate solution;

adding a surfactant selected from nonionic, anionic, cationic, and zwitterionic surfactants and combinations thereof;

optionally adding one or more stabilizers selected from fatty acids, fatty alcohols, alcohols, long chain fatty acid esters, long chain ethers, hydrophilic derivatives of fatty acids, polyvinylpyrrolidones, polyvinylethers, polyvinyl alcohols, hydrocarbons, hydrophobic polymers, moisture-absorbing polymers and mixtures thereof and incorporating the fibrate solution into a capsule. The method object of the present invention may use a solubilizers of fenofibrate selected from N-methyl-2-pyrrolidone, diethylene glycol monoethyl ether, propylene glycol mono- or diesters of caprylic acid, capric acid, lauric acid or other medium chain fatty acids or fatty acid mixtures, and combinations thereof.

The present process may additionally include the banding of the capsule to prevent leakage.

In an alternate embodiment of the present invention a method of preparation for a oral formulation of fenofibrate or fenofibrate derivative with an improved bioavailability comprising:

dissolving the fenofibrate, fenofibrate derivative or mixtures thereof in an appropriate volume of a fibrate solubilizers defined above, at least one surfactant and optionally one or more stabilizers to obtain a fenofibrate solution;

mixing the fenofibrate solution with an appropriate amount of a molten gelling agent to obtain a hot fenofibrate gel; and incorporating the fenofibrate gel into a capsule. The method object of the present invention may use a solubilizers of fenofibrate selected from N-methyl-2-pyrrolidone, diethylene glycol monoethyl ether, propylene glycol mono- or diesters of caprylic acid, capric acid, lauric acid or other medium chain fatty acids or fatty acid mixtures, and combinations thereof.

In an alternate embodiment of the present invention a method of preparation for a oral formulation of fenofibrate or fenofibrate derivative with an improved bioavailability comprising:

dissolving the fenofibrate, fenofibrate derivative or mixtures thereof in an appropriate volume of a fibrate solubilizers defined above, at least one surfactant and optionally one or more stabilizers to obtain a fenofibrate solution;

the liquid solution is mixed with appropriate amounts of an adsorbing powder (suitable adsorbing powders include but are limited to dibasic calcium phosphate, polysaccharides and PVP); to obtain a free flowing powder mixture; and incorporation of said free flowing powder mixture into a capsule. The method object of the present invention may use a solubilizers of fenofibrate selected from N-methyl-2-pyrrolidone, diethylene glycol monoethyl ether, propylene glycol mono- or diesters of caprylic acid, capric acid, lauric acid or other medium chain fatty acids or fatty acid mixtures, and combinations thereof.

The present invention also includes a commercial package containing a fenofibrate formulation containing a therapeutically effective dose of fenofibrate, a fenofibrate derivative or mixtures thereof dissolved solubilizer selected from $N-C_{1-4}$ alkyl derivative of 2-pyrrolidone, mono- or di- or poly-ethylene glycol monoethers, $C_{8-12}$ fatty acid mono- or di-esters of propylene glycol, or combinations thereof and one or more ionic or non-ionic surfactants. The formulation may further contain a stabilizer defined above. The commercial package further includes instructions for the use of the pharmaceutical formulation in the treatment of hypercholesterolaemias and hypertriglyceridaemias in mammals. If required, the pharmaceutical formulation is admixed with a pharmaceutically acceptable carrier, excipient or adjuvant. The pharmaceutical agent may be incorporated into a drug delivery device suitable for oral administration and enclosed in a pharmaceutical acceptable container.

The following examples illustrate the present invention in a manner of which it can be practiced but, as such, should not be construed as limitations upon the overall scope of the processes of this invention.

EXAMPLE 1

Liquid Formulation

Formulation PD0106-40B was prepared by first dissolving the active (fenofibrate) in appropriate amounts of NMP. Upon complete dissolution of the drug in NMP, the remaining excipients were added and the final solution was encapsulated in size 0 hard gelatin capsules. The filled capsules were then banded using a Quali-Seal lab top banding machine to prevent leakage of the fill contents from the capsules.

Formulation PD0106-50 was prepared similarly in that the drug was first dissolved in NMP and then an appropriate amount of a gelling agent such as polyglycolyzed glyceride (e.g. Gelucire 50/13) was added to this solution. The hot melt was encapsulated into size 1 hard gelatin capsules. The solution in the capsules congealed upon reaching room temperature and thus the final state of the fill material was semi-solid, gel-like, matter. This formulation is advantageous in that once processing step, namely leak proof banding, is eliminated from the manufacturing scheme.

TABLE 2

Composition of Typical Formulations of Fenofibrate

|  |  | PD0106-40B | | PD0106-50 | |
| --- | --- | --- | --- | --- | --- |
|  | Ingredients | A | B | A | B |
| Drug | Fenofibrate | 67 | 15 | 67 | 20 |
| Solubilizers | NMP | 89.4 | 20 | 67 | 20 |
|  | Captex 200 | 179 | 40 | — | — |
| Surfactant | Cremophor RH 40 | 11 | 2.5 | — | — |
|  | Span 80 | 11 | 2.5 | — | — |
| Gelling agent | Gelucire 44/14 | 89 | 20 | — | — |
|  | Gelucire 50/13 | — | — | 201 | 60 |

A = composition in mg per capsule
B = composition in % weight

TABLE 2-continued

Composition of Typical Formulations of Fenofibrate

|  | PD0106-40B | | PD0106-50 | |
|---|---|---|---|---|
| Ingredients | A | B | A | B |

Note:
Captex 200 is a trade name for Propylene Glycol Dicaprylate/Dicaprate and marketed by Abitec Corp.
Gelucire 44/14 and 50/13 are trade names for a mixture of mono-,di-and 10 triglycerides and mono-and di-fatty acid esters of polyethylene glycol and marketed by Gattefosse Corp.
Cremophor RH40 is a trade name for PEG-n-Hydrogenated Castor Oil and marketed by BASF Corp.
Span 80 is a trade name for sorbitan monooleate and marketed by ICI Chemical. Content uniformity tests were conducted by determining the amount of fenofibrate in each of 10 capsules (Samples A through J) using a high pressure liquid chromatography (HPLC) methodology specific for fenofibrate detection. The relative standard deviation (RSD) of the average of 10 capsules is then taken as an indicator of content uniformity with % RSD < 5.0 as passing.The content uniformity data is given in Table 2 below.

TABLE 3

Content Uniformity Data for
Fenofibrate Capsule Formulation

|  | PD0106-32B | |
|---|---|---|
| Sample | X | Y |
| A | 66.46 | 99.2 |
| B | 67.85 | 101.3 |
| C | 66.73 | 99.6 |
| D | 65.06 | 97.1 |
| E | 69.47 | 103.7 |
| F | 67.27 | 100.4 |
| G | 66.20 | 98.8 |
| H | 66.98 | 100.0 |
| I | 67.84 | 101.3 |
| J | 67.20 | 100.3 |
| Mean | 67.11 | 100.2 |
| % RSD |  | 1.74 |

X = weight (mg) per capsule
Y = percent label claim per capsule

EXAMPLE 2

Biologic Activity

Formulations tested were administered orally to dogs using 67 mg capsules of fenofibrate. Two formulations containing NMP as a solubilizer were tested in vivo as part of the dog study (n=5). The formulations were prepared similar to that described in example 1. Lipanthyl® (current marketed fenofibrate product) served as the reference formulation, and the two test formulations were liquid filled (PD0106-40B) and gel filled (PD0106-50) capsules.

TABLE 4

Plasma Concentrations of Fenofibrate in Fasted
Dogs after a 67 mg Dose

| Formulation (Fenofibrate Strength) | $C_{max}$ (µg/ml) | $T_{max}$ (hr) | $AUC_{0-24}$ (µg · hr/ml) | % Enhancement |
|---|---|---|---|---|
| Lipanthyl ® SD 67 mg | 1.88 0.97 | 1.6 0.9 | 11.08 9.42 | — |
| PD0106-40B SD 67 mg | 6.11 2.49 | 1.4 0.5 | 29.96 11.87 | 270 |

TABLE 4-continued

Plasma Concentrations of Fenofibrate in Fasted
Dogs after a 67 mg Dose

| Formulation (Fenofibrate Strength) | $C_{max}$ (µg/ml) | $T_{max}$ (hr) | $AUC_{0-24}$ (µg · hr/ml) | % Enhancement |
|---|---|---|---|---|
| PD0106-50 SD 67 mg | 3.60 1.06 | 0.9 0.2 | 18.11 3.65 | 164 |

* Enhancement values were calculated by $(AUC_{0-24(test)}/AUC_{0-24(Lipanthyl)}) \times 100$ The data summarized in Table 4. The mean $C_{max}$ for Lipanthyl®, PD016-40B, and PD0106-50 were 1.88, 6.11, and 3.60 µg/ml, respectively. The mean $AUC_{0-24}$ for Lipanthyl®, PD0106-40B, and PD0106-50 were 11.08, 29.96, and 18.11 µg.hr/ml, respectively. Both test formulations were effective in significantly increasing the $C_{max}$ and $AUC_{0-24}$ compared to Lipanthyl®.

Note:
Lipanthyl is a registered trademark of Groupe Fournier and is used as a reference formulation.

EXAMPLE 3

Semi-solid Fenofibrate Formulation

Formulations are prepared following the procedure outlined in Example 1.

TABLE 5

Examples of formulations of fenofibrate
in hard gelatin capsule:

| Ingredient | Amount | | |
|---|---|---|---|
| Fenofibrate | 150 mg (20% W/W) | 54 mg (20% W/W) | 54 mg (20% W/W) |
| NMP | 150 mg (20% W/W) | 54 mg (20% W/W) | 40.5 mg (15% W/W) |
| Gelucire 50/13 | 450 mg (60% W/W) | 162 mg (60% W/W) | 175.5 mg (65% W/W) |
| TOTAL | 750 mg | 270 mg | 270 mg |

EXAMPLE 4

Self-Emulsifying Formulations

A) Formulation PD0106-36 and PD0106-72

The formulations were prepared by first dispersing non-micronized fenofibrate in appropriate amounts of DGME. Upon complete wetting and dispersion of the drug in DGME, the remaining excipients were added and the final formulation was in the form of a solution. This solution was encapsulated in size 0 hard gelatin capsules. The filled capsules were then banded using a Quali-Seal lab top banding machine to prevent leakage of the fill contents from the capsules.

TABLE 6A

Composition of A Self-Emulsifying Formulation of Fenofibrate

|  |  | PD0106-72 | | PD0106-36 | |
| --- | --- | --- | --- | --- | --- |
| Ingredients | | A | B | A* | B |
| Drug | Fenofibrate | 54 | 15 | 67 | 15 |
| Solubilizers | Transcutol ® P (DGME) | 108 | 30 | 134 | 30 |
|  | Captex ® 200 | 162 | 45 | 201 | 45 |
| Surfactant | Labrasol ® | 18 | 5 | 22 | 5 |
|  | Span ® 80 | 18 | 5 | 22 | 5 |

*A = composition in mg per capsule
B = composition in % weight
Note:
Transcutol ® P is a trade name for Diethylene Glycol Monoethyl Ether, USP/NF, and is marketed by Gattefosse Corp.
Captex ® 200 is a trade name for Propylene Glycol Dicaprylate/Dicaprate and marketed by Abitec Corp.
Labrasol ® is a trade name for Caprylocaproyl Macrogolglycerides, EP, and is marketed by Gattefosse Corp.
Span ® 80 is a trade name for sorbitan monooleate and marketed by ICI Chemical.

Content uniformity tests were conducted by determining the amount of fenofibrate in each of 10 capsules (Samples A through J) using a high pressure liquid chromatography (HPLC) methodology specific for fenofibrate detection. The relative standard deviation (RSD) of the average of 10 capsules is then taken as an indicator of content uniformity with % RSD<5.0 as passing. The content uniformity data is given in Table 6C below.

B) Formulation PD0106-40B

Formulation PD0106-40B was prepared by first dissolving the non-micronized fenofibrate in appropriate amounts of NMP. Upon complete dissolution of the drug in NMP, the remaining excipients were added and the final solution was encapsulated in size 0 hard gelatin capsules. The filled capsules were then banded using a Quali-Seal lab top banding machine to prevent leakage of the fill contents from the capsules.

TABLE 6B

Composition of A S lf-Emulsifying PD0106-40B Formulation of Non-Micronized Fenofibrate

|  |  | PD0106-40B | |
| --- | --- | --- | --- |
| Ingredients | | A | B |
| Drug | Fenofibrate | 67 | 15 |
| Solubilizers | NMP | 89.4 | 20 |
|  | Captex ® 200 | 179 | 40 |
| Surfactants | Gelucire ® 44/14 | 89 | 20 |
|  | Cremophor ® RH 40 | 11 | 2.5 |
|  | Span ® 80 | 11 | 2.5 |

*A = composition in mg per capsule
B = composition in % weight
Note:
Captex ® 200 is a trade name for Propylene Glycol Dicaprylate/Dicaprate and marketed by Abitec Corp.
Gelucire ® 44/14 and 50/13 are trade names for a mixture of mono-, di- and triglycerides and mono-and di-fatty acid esters of polyethylene glycol and marketed by Gattefosse Corp.
Cremophor ® RH40 is a trade name for PEG-n-Hydrogenated Castor Oil and marketed by BASF Corp.
Span ® 80 is a trade name for sorbitan monooleate and marketed by ICI Chemical.

TABLE 6C

Content Uniformity Data for Fenofibrate Capsule Formulation

|  | PD0106-36 | |
| --- | --- | --- |
| Sample | mg | % |
| A | 63.00 | 94.0 |
| B | 71.75 | 107.1 |
| C | 71.75 | 107.1 |
| D | 65.30 | 97.5 |
| E | 65.91 | 98.4 |
| F | 70.59 | 105.4 |
| G | 72.57 | 108.3 |
| H | 68.25 | 101.90 |
| I | 65.03 | 97.1 |
| J | 67.46 | 100.7 |
| Mean | 68.16 | 101.8 |
| % RSD | | 4.92 |

TABLE 6D

Self-emulsifying system with NMP/Captex 200 as the solubilizer

|  | PD0106-77A* | |
| --- | --- | --- |
| Ingredients | A | B (mg) |
| Fenofibrate | 15% | 300 |
| NMP | 30% | 600 |
| Captex 200 | 45% | 900 |
| Labrasol | 5% | 100 |
| Span 80 | 5% | 100 |

*Formulation in both LiCaps (CAPSUGEL) and Conisnaps (CAPSUGEL)
Note:
Transcutol ® P is a trade name for Diethylene Glycol Monoethyl Ether, USP/NF, and is marketed by Gattefosse Corp.

TABLE 6E

Self-emulsifying system with NMP/Transcutol/ Captex 200 mixture as the solubilizer

|  |  | PD0106-77C* | |
| --- | --- | --- | --- |
| Ingredients | | A | B (mg) |
| Drug | Fenofibrate | 15% | 300 |
| Solubilizer | Transcutol | 24% | 480 |
|  | NMP | 6% | 120 |
|  | Captex 200 | 45% | 900 |
| Surfactants | Labrasol | 5% | 100 |
|  | Span 80 | 5% | 100 |

*Formulation in both LiCaps (CAPSUGEL) and Conisnaps (CAPSUGEL)

TABLE 6F

Self-emulsifying system with NMP/Transcutol/ Captex 200 mixture as the solubilizer

|  | PD0106-77D* | |
| --- | --- | --- |
| Ingredients | A | B (mg) |
| Fenofibrate | 15% | 300 |
| Transcutol | 15% | 300 |
| NMP | 15% | 300 |
| Captex 200 | 45% | 900 |
| Labrasol | 5% | 100 |
| Span 80 | 5% | 100 |

*Formulation in both LiCaps (CAPSUGEL) and Conisnaps (CAPSUGEL)

TABLE 6G

Self-emulsifying system with NMP/Transcutol/
fatty acids/Captex 200 mixture as the solubilizer

| | PD0106-77G* | |
|---|---|---|
| Ingredients | A | B (mg) |
| Fenofibrate | 15% | 300 |
| Transcutol | 14% | 280 |
| NMP | 14% | 280 |
| Captex 200 | 45% | 900 |
| Labrasol | 5% | 100 |
| Capric acid | 1% | 20 |
| Caprylic acid | 1% | 20 |
| Span 80 | 5% | 100 |

*Formulation in both LiCaps (CAPSUGEL) and Conisnaps (CAPSUGEL)

EXAMPLE 5

In Vivo Activity of Self-Emulsifying Formulation

Formulations tested were administered orally to dogs using 67 mg capsules of fenofibrate. The self-emulsifying formulation of Example 1 (Table 1A) was tested in vivo as part of the dog study (n=5). Lipanthyl® 67 mg (current marketed fenofibrate product) served as the reference formulation, and the test formulation was liquid filled hard gelatin capsule.

The data summarized in Table 7.

TABLE 7

Plasma Concentrations of Fenofibrate in Fasted Dogs after a 67 mg Dose

| Formulation | $C_{max}$ (μg/ml) | $T_{max}$ (hr) | $AUC_{0-24}$ (μg · hr/ml) | % Enhancement* |
|---|---|---|---|---|
| Lipanthyl ® | 1.88 | 1.6 | 11.08 | — |
| SD | 0.97 | 0.9 | 9.42 | |
| PD0106-36 | 4.17 | 1.1 | 24.17 | 218 |
| SD | 1.83 | 0.5 | 7.96 | |

The mean $C_{max}$ for Lipanthyl® and PD0106-36 were 1.88 and 4.17 μg/ml, respectively. The mean $AUC_{0-24}$ for Lipanthyl® and PD0106-36 were 11.08 and 24.17 μg.hr/ml, respectively. The test formulation was effective in significantly increasing the $C_{max}$ and $AUC_{0-24}$ compared to Lipanthyl®.

Note:
Lipanthyl ® is a marketed product of Groupe Fournier and is used as a reference formulation.

EXAMPLE 6

Self-Emulsifying Properties

To evaluate the behavior of the self-emulsifying formulation as it becomes exposed to aqueous media, five grams of various fenofibrate solution formulations were prepared and known amounts of water were added to the respective formulas. The compositions of the formulations along with the outcome of the water addition are shown in Table 8.

TABLE 8

Effect of water addition on various liquid fenofibrate formulations

| FORMULATION* | COMPOSITION (% W/W) | OBSERVATION |
|---|---|---|
| PD0106-61A | Fenofibrate, 20%<br>Transcutol P, 80% | Upon addition of only 1 ml of water, fenofibrate crashed out of solution and large crystal precipitates appeared. |
| PD0106-61B | Fenofibrate, 15%<br>Transcutol P, 30%<br>Captex 200, 45%<br>Labrasol, 5%<br>Span 80, 5% | Upon addition of water the self-emulsifying formulation turned into a white emulsion with no precipitates forming even after addition of 11 ml of water, which was more than twice the volume of the starting formulation. |
| PD0106-61C | Fenofibrate, 6.25%<br>Transcutol P, 93.75% | Upon addition of only 2 ml of water, fenofibrate crashed out of solution and large crystal precipitates appeared. |
| PD0106-65A | Fenofibrate, 15%<br>Transcutol P, 75%<br>Labrasol, 5%<br>Span 80, 5% | Upon addition of only 1 ml of water, fenofibrate crashed out of solution and large crystal precipitates appeared. |
| PD0106-65B | Fenofibrate, 15%<br>Captex 200, 75%<br>Labrasol, 5%<br>Span 80, 5% | Upon addition of only 2 ml of water, fenofibrate crashed out of solution and crystalline precipitates appeared. |
| PD0106-65C | Fenofibrate, 15%<br>Captex 200, 45%<br>N-methyl-2-pyrrolidone (NMP), 30%<br>Labrasol, 5%<br>Span 80, 5% | Upon addition of water the self-emulsifying formulation turned into a white emulsion with no precipitates forming even after addition of 5 ml of water. |
| PD0106-65D | Fenofibrate, 15%<br>NMP, 75%<br>Labrasol, 5%<br>Span 80, 5% | Upon addition of only 2 ml of water, fenofibrate crashed out of solution and crystalline precipitates appeared. |
| PD0106-65E | Fenofibrate, 15%<br>Transcutol P, 45%<br>NMP, 30% | Upon addition of only 2 ml of water, fenofibrate crashed out of solution and crystalline precipitates appeared. |

TABLE 8-continued

Effect of water addition on various liquid fenofibrate formulations

| FORMULATION* | COMPOSITION (% W/W) | OBSERVATION |
|---|---|---|
| PD0106-66 | Labrasol, 5%<br>Span 80, 5%<br>Fenofibrate, 15%<br>Transcutol, 80%<br>Labrasol, 5% | Upon addition of only 1 ml of water, fenofibrate crashed out of solution and large crystal precipitates appeared. |

*All formulations were in complete solution before water addition
Note:
Transcutol ® P is a trade name for Diethylene Glycol Monoethyl Ether, USP/NF, and is marketed by Gattefosse Corp.
Captex ® 200 is a trade name for Propylene Glycol Dicaprylate/Dicaprate and marketed by Abitec Corp.
Labrasol ® is a trade name for Caprylocaproyl Macrogolglycerides, EP, and is marketed by Gattefosse Corp.
Span ® 80 is a trade name for sorbitan monooleate and marketed by ICI Chemical.

The self-emulsifying formulations (PD0106-61B and PD0106-65C) did not crash in presence of excessive amounts of water, whereas all other formulations containing various solutions of fenofibrate severely crashed out of solution by forming large crystalline particulates upon addition of 1 or 2 ml of water. Our self-emulsifying formulations are superior to solution formulations containing the drug and a solubilizer.

EXAMPLE 7

The formulations were prepared as follow: NMP and Transcutol P were added to a known amount of fenofibrate and vortex mixed. The mixture was heated until it became clear and vortex mixed. Then Captex 200, Labrasol and other surfactants were added to the formulation and vortex mixed. For 75, SLS was premixed with NMP and Transcutol P before being added to fenofibrate.

TABLE 9

Self-emulsifying formulations of Fenofibrate containing non-ionic and ionic surfactants

| | | Ingredient | 75 | 9 |
|---|---|---|---|---|
| Drug | | Fenofibrate | 14.3 | 15 |
| Solubilizers | | NMP | 33.3 | 15 |
| | | Transcutol P | — | 15 |
| | | Captex 200 | 42.9 | 45 |
| Surfactants | Non-ionic | Labrasol | 4.8 | 8 |
| | | Span 80 | 4.3 | — |
| | Ionic | SLS | — | 2 |
| | | Lecithin | 0.48 | — |

Note:
numbers are w/w %

EXAMPLE 8

Self-emulsifying Formulations of Fenofibrate Stabilizers

NMP and Transcutol P were added to a known amount of fenofibrate and vortex mixed. If fenofibrate does not dissolve completely, the mixture was heated until it became clear and vortex mixed. Then Captex 200, Labrasol and other solubilizers and surfactants were added to the formulation and vortex mixed. Stabilizers were then mixed with the formulation to yield the stabilized formulations. Stabilizers with melting points higher than ambient temperature were melted first in a separate container then mixed rapidly with the formulations.

TABLE 10

Self-emulsifying formulations of Fenofibrate containing stabilizers

| | Ingredient | 75 | PD0106-94 | PD0106-95 | PD0106-91 | 13 | 14 | 15 | 77 | 29 | St-2-8 |
|---|---|---|---|---|---|---|---|---|---|---|---|
| Drug | Fenofibrate | 28.6 | 13 | 13.6 | 13.6 | 15 | 15 | 15 | 27.1 | 15 | 23.9 |
| Solubilizers | NMP | 26.3 | 30.4 | 13.6 | 5.4 | 20 | 20 | 5 | 27.7 | 4 | 26.7 |
| | Transcutol P | — | — | 13.6 | 21.8 | — | — | 25 | — | 22 | — |
| | Captex 200 | 33.8 | 39.1 | 40.9 | 40.9 | 45 | 45 | 40 | 35.6 | 40 | 17.1 |
| | Capmul PG-8 | — | — | — | — | — | — | — | — | — | 17.1 |
| Surfactants Non-ionic | Labrasol | 3.8 | 8.7 | 9.1 | 9.1 | 5 | 5 | 5 | 4 | 10 | 7.6 |
| | Span 80 | 3.4 | 4.4 | 4.6 | 4.6 | 5 | 5 | 5 | 4 | 5 | 3.8 |
| Ionic | Phospholipid | 0.33 | — | — | — | — | — | — | — | — | — |
| Stabilizers | Oleic Acid | 3.8 | 4.4 | 4.6 | 4.6 | — | — | — | — | — | 3.8 |
| | Capric Acid | — | — | — | — | — | — | — | — | 2 | — |
| | Caprylic Acid | — | — | — | — | — | — | — | — | 2 | — |
| | Kollidon 12PF | — | — | — | — | — | — | — | 1.6 | — | — |
| | Carnauba Wax | — | — | — | — | — | 10 | 5 | — | — | — |

TABLE 10-continued

Self-emulsifying formulations of Fenofibrate containing stabilizers

| Ingredient | 75 | PD0106-94 | PD0106-95 | PD0106-91 | 13 | 14 | 15 | 77 | 29 | St-2-8 |
|---|---|---|---|---|---|---|---|---|---|---|
| Microcrystalline Wax | — | — | — | — | 10 | — | — | — | — | — |

Note:
numbers are w/w %

EXAMPLE 10

Stable Self-Emulsifying Formulations of Fenofibrate with Lower Levels of Solvents Using Stabilizers to Prevent Crystal Growth Transcutol P was added to a known amount of fenofibrate and vortex mixed. If fenofibrate does not dissolve completely, the mixture was heated until it became clear and vortex mixed. Then Captex 200, Labrasol and other solubilizers and surfactants were added to the formulation and vortex mixed. Stabilizers were then mixed with the formulation to yield the stabilized formulations. Stabilizers with melting points higher than ambient temperature were melted first in a separate container then mixed rapidly with the formulations.

All formulations in Table 11 were stable and no crystal growth was observed.

EXAMPLE 11

Crystal Growth from Self-Emulsifying Formulations of Fenofibrate with and without Stabilizers Transcutol P was added to a known amount of fenofibrate and vortex mixed. If fenofibrate does not dissolve completely, the mixture was heated until it became clear and vortex mixed. Then Captex 200, Labrasol and other solubilizers and surfactants were added to the formulation and vortex mixed. Stabilizers were then mixed with the formulation to yield the stabilized formulations. Stabilizers with melting points higher than ambient temperature were melted first in a separate container then mixed rapidly with the formulations.

TABLE 11

Stable self-emulsifying formulations of Fenofibrate with lower levels of solvents using stabilizers to prevent crystal growth

|  | Ingredient | PD0106-109A | PD0106-94 | PD0106-109C | PD0106-109E | PD0106-109F | PD0106-101D | PD0106-103B | PD0106-107B |
|---|---|---|---|---|---|---|---|---|---|
| Drug | Fenofibrate | 13.23 | 13 | 13.25 | 13.23 | 12.94 | 9.52 | 12.09 | 13.58 |
| Solubilizers | Transcutol P | 14.27 | 12.20 | 10.55 | 16.51 | 8.74 | — | — | — |
|  | Captex 200 | 51.78 | 51.78 | 52.75 | 52.69 | 52.96 | 61 | 49.45 | 55.56 |
|  | Capmul PG-8 | — | — | — | — | — | — | 10.99 | 12.35 |
| Surfactants | Labrasol | 5.75 | 5.75 | 5.86 | 5.85 | 5.71 | 6.78 | 5.49 | 6.17 |
|  | Span 80 | 5.75 | 5.75 | 5.86 | 5.85 | 5.71 | 6.78 | 5.49 | 6.17 |
| Stabilizers | Ethanol | — | — | — | — | 5.71 | 9.15 | 5.49 | 6.17 |
|  | Oleic Acid | 9.21 | 11.51 | 11.72 | 5.85 | 8.24 | 6.78 | 10.99 | — |

Note:
numbers are w/w %

TABLE 12

Crystal growth from Self-emulsifying formulations of Fenofibrate with and without stabilizers

|  | Ingredient | PD0106-104B | PD0106-109F | PD0106-103A | PD0106-107B | PD0106-103B |
|---|---|---|---|---|---|---|
| Drug | Fenofibrate | 14.05 | 12.94 | 13.04 | 13.58 | 12.09 |
| Solubilizers | Transcutol P | 9.48 | 8.74 | — | — | — |
|  | Captex 200 | 42.15 | 52.96 | 48.91 | 55.56 | 49.45 |
|  | Capmul PG-8 | 21.66 | — | 10.87 | 12.35 | 10.99 |
| Surfactants | Labrasol | 6.32 | 5.71 | 5.43 | 6.17 | 5.49 |
|  | Span 80 | 6.31 | 5.71 | 5.43 | 6.17 | 5.49 |
| Stabilizers | Oleic Acid | — | 5.71 | 10.87 | 6.17 | 5.49 |
|  | Ethanol | — | 8.24 | 5.43 | — | 10.99 |
| Saturation factor* |  |  | 1.54 | 1.58 | 1.71 | 1.67 | 1.57 |
| Crystal growth |  | Yes | No | No | No | No |

TABLE 12-continued

Crystal growth from Self-emulsifying formulations of Fenofibrate with and without stabilizers

| Ingredient | PD0106-104B | PD0106-109F | PD0106-103A | PD0106-107B | PD0106-103B |
|---|---|---|---|---|---|

Note:
numbers are w/w %
*Saturation factor = Drug amount used in formulation/Sum of maximum fenofibrate solubility in each excipient fractions. (The higher the saturation factor, the more fenofibrate used over the saturation point calculated from the solubility of fenofibrate in neat excipients).

EXAMPLE 12

Self-emulsifying Formulations Containing Various Amount of Solvents with Enhanced Fenofibrate Solubility Transcutol P was added to a known amount of fenofibrate (in excess) and vortex mixed. Then Captex 200, Labrasol and other solubilizers and surfactants were added and the mixtures were vortex mixed. Stabilizers were added according the procedures in Example 10. The resultant formulations were further mixed in a rotary mixer overnight then filtered through a 1-micron syringe filter. The amounts of fenofibrate in formulations were analyzed by HPLC.

The term "rank of fenofibrate solubility" means the rank of ability of that particular formulation in dissolving fenofibrate and forming a stable SEDDS formula.

TABLE 13

Self-emulsifying formulations containing various amount of solvents with enhanced fenofibrate solubility

| | Ingredient | 1 | 3 (31) | 7 (7 PD0106-77) | 10 (3) | 4 (71) | 5 (77) | 9 (75) | 4 | 5 |
|---|---|---|---|---|---|---|---|---|---|---|
| Drug | Fenofibrate dissolved | 139** | 152** | 194** | 211** | 260** | 260** | 260** | 281** | 291** |
| Solubilizers | NMP | — | 6 | 15 | 20 | 35 | 35 | 35 | 45 | 50 |
| | Transcutol P | 30 | 24 | 15 | — | — | — | — | — | — |
| | Captex 200 | 45 | 45 | 45 | 45 | 45 | 45 | 45 | 45 | 45 |
| Surfactants Non-ionic | Labrasol | 5 | 5 | 5 | 5 | 5 | 5 | 5 | 5 | 5 |
| | Span 80 | 5 | 5 | 5 | 5 | 5 | 5 | 4.5 | 5 | 5 |
| ionic | Phospholipid | — | — | — | — | — | — | 0.5 | — | — |
| Stabilizers | Oleic Acid | — | 3 | — | — | 5 | — | 5 | 5 | 5 |
| | Kollidon 12PF | — | — | — | — | — | 2 | — | — | — |
| | Caprylic Acid | — | — | 1 | 5 | — | — | — | — | — |
| | Capric Acid | — | — | 1 | 5 | — | — | — | — | — |

Note:
numbers are in parts, unless otherwise indicated
**mg/ml of fenofibrate in formulation analyzed by HPLC, which indicates the relative rank of fenofibrate solubility among these formulations.

EXAMPLE 13

Pharmacokinetic Study of Self-Emulsifying Fenofibrate Formulations in Canine in Fasted State and Fed State Compared to Commercially Available Fenofibrate Formulations All dogs received a dose of each test formulation and Tricor under fed and fasted conditions with a 7-day washout period between each dose (a total of eight periods). The study was conducted using six healthy beagles that were given the test formulations as a single hard gelatin capsule. The fenofibrate formulation used was PD0106-72 (see Example 4). Following each dose, PK samples were drawn at the following time points: pre-dose, and 0.25, 0.5, 1.0, 1.5, 2, 3, 4, 6, 9, 15, 24 and 36 hours post-dose. Samples were analyzed for fenofibric acid using a validated LC/UV method.

TABLE 14

Pharmacokinetic study of self-emulsifying fenofibrate formulations in canin in fasted state and fed state compared to commercially available fenofibrate formulations

| | Fasted State | | Fed State | |
|---|---|---|---|---|
| | TriCor ® | PD0106-72 | TriCor ® | PD0106-72 |
| $T_{max}$ | 1.40 | 1.58 | 1.08 | 1.00 |
| $C_{max}$ | 0.82 | 3.92 | 6.16 | 4.26 |
| AUC | 7.50 | 22.42 | 31.57 | 31.94 |
| Relative Bioavailability*** | 23.7% | 71% | 100% | 100% |
| Lambda z**** | 0.0667 | 0.0640 | 0.0453 | 0.0589 |
| % Enhancement (fasted) | 100 | 300% | — | — |

TABLE 14-continued

Pharmacokinetic study of self-emulsifying fenofibrate
formulations in canin in fasted state and fed state compared
to commercially available fenofibrate formulations

| | Fasted State | | Fed State | |
|---|---|---|---|---|
| | TriCor® | PD0106-72 | TriCor® | PD0106-72 |

***Relative bioavailabilty is calculated from AUC using TriCor® control in fed state as 100%.
****Lambda z is the elimination rate constant, the term describes the terminal Log-Linear phase of a plot of plasma concentration vs time.

TriCor® formulation showed severe food effect while PD0106-72 (see Example 4) showed significant reduction in the food effect.

The invention claimed is:

1. A method of treating an endogenous condition selected from the group consisting of hyperlipidaemias, hypercholesterolaemias and hypertriglyceridaemias in a mammal comprising the administration of an oral self-emulsifying pharmaceutical formulation of a fibrate with improved oral bioavailability, wherein said formulation consists essentially of a fibrate dissolved in at least one fibrate solubilizer, at least one surfactant and at least one stabilizer,
   wherein said fibrate is selected from the group consisting of fenofibrate, derivative of fenofibrate and mixtures thereof,
   wherein said at least one fibrate solubilizer is selected from the group consisting of an N-alkyl derivative of 2-pyrrolidone, monoethylene glycol monoethers, diethylene glycol monoethers, higher-ethylene glycol monoethers, polyethylene glycol monoethers, $C_{8-12}$ fatty acid mono- or diesters of propylene glycol, and combinations thereof;
   wherein said at least one or more surfactant is selected from the group consisting of nonionic, anionic, cationic, and zwitterionic surfactants and combinations thereof;
   wherein the fibrate to the fibrate solubilizer weight ratio is between about 1:1 and about 1:16,
   and wherein said at least one stabilizer is present in an amount sufficient to prevent the crystal growth of the fibrate, wherein fibrate remains in solution in said formulation and no crystallization of fibrate is observed for at least 24 hours, wherein the amount of said solubilizer is between about 20% to about 80% by weight of the formulation, and wherein the amount of said stabilizer is up to about 30% by weight of the formulation.

2. A method according to claim 1, wherein said at least one stabilizer is selected from the group consisting of fatty acids, fatty alcohols, alcohols, long chain fatty acid esters, long chain ethers, hydrophilic derivatives of fatty acids, polyvinylpyrrolidones, polyvinylethers, polyvinyl alcohols, hydrocarbons, hydrophobic polymers, and moisture-absorbing polymers.

3. A method according to claim 1 wherein the weight ratio of the fibrate to the stabilizer is between about 50:1 to about 1:10.

4. A method according to claim 1 wherein said at least one fibrate solubilizer is selected from the group consisting of N—$C_{1-4}$ alkyl derivative of 2-pyrrolidone, monoethylene glycol monoethers, diethylene glycol monoethers, higher-ethylene glycol monoethers, polyethylene glycol monoethers, $C_{8-12}$ fatty acid mono- or diesters of propylene glycol, and combinations thereof.

5. A method according to claim 1 wherein said at least one surfactant is present in an amount that is between about 2% to about 25% by weight of the formulation.

6. A method according to claim 1 wherein the solubilizer is selected from the group consisting of N—$C_{1-4}$ alkyl derivatives of 2-pyrrolidones, monoethylene glycol monoethers, diethylene glycol monoethers, higher-ethylene glycol monoethers, polyethylene glycol monoethers, $C_{8-12}$ fatty acid mono- or diesters of propylene glycol, and combinations thereof.

7. A method according to claim 6 wherein said solubilizer comprises:
   (a) a first component selected from the group consisting of an N—$C_{1-4}$ alkyl derivative of 2-pyrrolidone, -monoethylene glycol monoether, diethylene glycol monoether, other higher-ethylene glycol monoether, polyethylene glycol monoether, or combinations thereof; and
   (b) a second component selected from the group consisting of one or more $C_{8-12}$ fatty acid mono- or diesters of propylene glycol; and
   wherein the weight ratio of said first component and said second component is between about 100:1 to about 1:100.

8. A method according to claim 6 wherein said solubilizer is a $C_{8-12}$ fatty acid monoester of propylene glycol, a $C_{8-12}$ fatty acid diester of propylene glycol, or combinations thereof.

9. A method according to claim 1 wherein said solubilizer comprises an N—$C_{1-4}$ alkyl derivative of 2-pyrrolidone selected from the group consisting of N-methyl-2-pyrrolidone, N-ethyl-2-pyrrolidone, N-propyl-2-pyrrolidone, N-isopropyl-2-pyrrolidone, N-butyl-2-pyrrolidone, and N-(2-hydroxyethyl)-2-pyrrolidone and mixtures thereof.

10. A method according to claim 9 wherein said solubilizer comprises N-methyl-2-pyrrolidone.

11. A method according to claim 1, wherein said solubilizer comprises an ether selected from the group consisting of diethylene glycol monoethyl ether, diethylene glycol monobutyl ether, ethyleneglycol monoethyl ether, ethyleneglycol monobutyl ether, other higher-ethylene glycol monoethers, and polyethylene glycol monoethers.

12. A method formulation according to claim 1 wherein said fibrate solubilizer comprises a combination of N-methyl-2-pyrrolidone and diethylene glycol monoethyl ether,
   wherein the weight ratios of N-methyl-2-pyrrolidone to diethylene glycol monoethyl ether is between about 100:1 and about 1:100.

13. A method according to claim 6 wherein said stabilizer selected from the group consisting of ethanol, oleic acid, caprylic acid, capric acid, polyvinylpyrrolidone, waxes, and combinations thereof.

14. A method of treating a subject suffering from endogenous hyperlipidaemia, hypercholesterolaemia and/or hypertriglyceridaemia, comprising administering to the subject a self-emulsifying oral pharmaceutical formulation with improved bioavailability, wherein said formulation consists essentially of:
   a therapeutically effective amount of fenofibrate or a fenofibrate derivative;
   at least one surfactant;
   about 20% to about 80% one or more fibrate solubilizers selected from N-alkyl derivative of 2-pyrrolidone, monoethylene glycol monoethers, diethylene glycol monoethers, higher-ethylene glycol monoethers, polyethylene glycol monoethers, $C_{8-12}$ fatty acid mono- or diesters of propylene glycol, and combinations thereof; and up to about 30% one or more stabilizers;
wherein the fibrate to solubilizer weight ratio is between about 1:1 and about 1:100 and the saturation factor is between about 1.05 and about 2.5 and the stabilizer is present in sufficient amounts to prevent crystal growth.

15. A method according to claim 1, wherein said formulation has a $C_{max}$ that is at least 1.2 times that of Lipanthyl® or TriCor®, or has an $AUC_{0-\infty}$ that is at least 1.5 times that of Lipanthyl® or TriCor® when administered to mammals in the fasted state.

16. A method according to claim 14, wherein said formulation has a $C_{max}$ that is at least 1.2 times that of Lipanthyl® or TriCor®, or has an $AUC_{0-\infty}$ that is at least 1.5 times that of Lipanthyl® or TriCor® when administered to mammals in the fasted state.

17. A method of treating a subject suffering from endogenous hyperlipidaemia, hypercholesterolaemia and/or hypertriglyceridaemia, comprising administering to the subject a fibrate formulation, wherein said formulation consists essentially of a fibrate dissolved in at least one fibrate solubilizer, at least one surfactant and, at least one stabilizer,
wherein said at least one fibrate solubilizer is selected from the group consisting of N-alkyl derivative of 2-pyrrolidone, monoethylene glycol monoethers, diethylene glycol monoethers, higher-ethylene glycol monoethers, polyethylene glycol monoethers, $C_{8-12}$ fatty acid mono- or diesters of propylene glycol, and combinations thereof;
wherein said at least one surfactant is selected from the group consisting of at least one ionic or non-ionic surfactant and combinations thereof; and
wherein the fibrate is between about 5 W/W % and about 40 W/W %, the fibrate solubilizer is between about 20 W/W % and about 80 W/W %; the surfactant is between about 2 W/W %, and about 25 W/W %; and stabilizer is between about 0 W/W % and 30 W/W %; and the stabilizer is present in an amount sufficient to prevent the crystal growth of the fibrate.

18. A method according to claim 17, wherein said formulation has a $C_{max}$ that is at least 1.2 times that of Lipanthyl® or TriCor® or the $AUC_{0-}$ is at least 1.5 times that of Lipanthyl® or TriCor® when administered to mammals in the fasted state.

19. A method according to claim 18, wherein said formulation has a saturation factor of between about 1.05 and 2.5.

* * * * *